US010281496B2

(12) United States Patent
Buck et al.

(10) Patent No.: US 10,281,496 B2
(45) Date of Patent: *May 7, 2019

(54) ELECTROSURGICAL GENERATORS AND SENSORS

(71) Applicant: COVIDIEN LP, Mansfield, MA (US)

(72) Inventors: Dean C. Buck, Loveland, CO (US); Edward L. Brannan, Erie, CO (US); Mark A. Johnston, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 393 days.

This patent is subject to a terminal disclaimer.

(21) Appl. No.: 14/557,557

(22) Filed: Dec. 2, 2014

(65) Prior Publication Data

US 2016/0154034 A1 Jun. 2, 2016

(51) Int. Cl.
| | | |
|---|---|---|
| G01R 15/18 | (2006.01) |
| A61B 18/00 | (2006.01) |
| A61B 18/12 | (2006.01) |
| A61B 18/14 | (2006.01) |

(52) U.S. Cl.
CPC .......... *G01R 15/18* (2013.01); *A61B 18/1206* (2013.01); *A61B 18/1402* (2013.01); *A61B 18/1445* (2013.01); *A61B 2018/0066* (2013.01); *A61B 2018/00642* (2013.01); *A61B 2018/00648* (2013.01); *A61B 2018/00702* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01)

(58) Field of Classification Search
CPC ................. G01R 15/181; A61B 18/1233
See application file for complete search history.

(56) References Cited

U.S. PATENT DOCUMENTS

| | | | |
|---|---|---|---|
| 3,252,052 | A | 5/1966 | Nash |
| 3,431,487 | A | 3/1969 | Savage |
| 3,601,126 | A | 8/1971 | Estes |
| 3,683,923 | A | 8/1972 | Anderson |
| 3,697,808 | A | 10/1972 | Lee |
| 3,885,569 | A | 5/1975 | Judson |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

European Search Report, dated May 10, 2016, corresponding to European Application No. 15191339.9; 10 pages.

(Continued)

*Primary Examiner* — Dixomara Vargas
*Assistant Examiner* — Adam S Clarke

(57) ABSTRACT

A sensor for sensing current includes a current sensor coil and at least one active lead and at least one return lead. The current sensor coil includes an outer coil and an inner coil coupled to and disposed within the outer coil. The at least one active lead and the at least one return lead pass through the current sensor coil opening. The current sensor coil is configured to output a differential signal indicative of a current within the at least one active lead and the at least one return lead.

17 Claims, 21 Drawing Sheets

(56) References Cited

U.S. PATENT DOCUMENTS

| | | | |
|---|---|---|---|
| 3,913,583 A | 10/1975 | Bross | |
| 4,102,341 A | 7/1978 | Ikuno et al. | |
| 4,263,549 A * | 4/1981 | Toppeto | G01R 15/185 324/127 |
| 4,437,464 A | 3/1984 | Crow | |
| 4,569,345 A | 2/1986 | Manes | |
| 4,754,757 A | 7/1988 | Feucht | |
| 5,067,953 A | 11/1991 | Feucht | |
| 5,152,762 A | 10/1992 | McElhenney | |
| 5,312,401 A * | 5/1994 | Newton | A61B 18/1233 606/35 |
| 5,414,400 A | 5/1995 | Gris et al. | |
| 5,442,280 A | 8/1995 | Baudart | |
| 5,540,684 A | 7/1996 | Hassler, Jr. | |
| 5,793,196 A | 8/1998 | White | |
| 5,817,091 A | 10/1998 | Nardella et al. | |
| 5,830,212 A | 11/1998 | Cartmell et al. | |
| 5,852,395 A | 12/1998 | Bosco et al. | |
| 6,094,044 A | 7/2000 | Kustera et al. | |
| 6,313,623 B1 | 11/2001 | Kojovic et al. | |
| 6,440,157 B1 | 8/2002 | Shigezawa et al. | |
| 6,511,478 B1 | 1/2003 | Burnside et al. | |
| 6,624,624 B1 | 9/2003 | Karrer et al. | |
| 6,680,608 B2 | 1/2004 | Kojovic | |
| 6,731,193 B2 | 5/2004 | Meier et al. | |
| 6,791,341 B2 | 9/2004 | Shenai et al. | |
| 6,822,547 B2 | 11/2004 | Saito et al. | |
| 6,825,650 B1 | 11/2004 | McCormack et al. | |
| 6,963,195 B1 * | 11/2005 | Berkcan | G01R 15/181 324/117 R |
| 6,979,329 B2 | 12/2005 | Burnside et al. | |
| 7,010,438 B2 | 3/2006 | Hancock et al. | |
| 7,041,096 B2 | 5/2006 | Malis et al. | |
| 7,072,779 B2 | 7/2006 | Hancock et al. | |
| 7,106,162 B2 | 9/2006 | Saito | |
| 7,164,263 B2 | 1/2007 | Yakymyshyn et al. | |
| 7,227,441 B2 | 6/2007 | Skendzic et al. | |
| 7,227,442 B2 | 6/2007 | Skendzic | |
| 7,274,186 B2 | 9/2007 | Yakymyshyn et al. | |
| 7,279,884 B2 | 10/2007 | Yakymyshyn et al. | |
| 7,279,885 B2 | 10/2007 | Yakymyshyn et al. | |
| 7,307,410 B2 | 12/2007 | Shiokawa et al. | |
| 7,321,226 B2 | 1/2008 | Yakymyshyn et al. | |
| D574,323 S | 8/2008 | Waaler | |
| 7,474,192 B2 | 1/2009 | Skendzic et al. | |
| 7,492,162 B2 | 2/2009 | Hachisuka et al. | |
| 7,545,138 B2 | 6/2009 | Wilkerson et al. | |
| 7,564,233 B2 | 7/2009 | Kojovic | |
| 7,579,824 B2 | 8/2009 | Rea et al. | |
| 7,598,748 B2 | 10/2009 | Hachisuka et al. | |
| 7,613,578 B2 | 11/2009 | Hagmann | |
| 7,638,999 B2 | 12/2009 | Kojovic et al. | |
| 7,728,578 B2 | 6/2010 | Etter et al. | |
| 7,736,359 B2 | 6/2010 | McPherson | |
| 7,746,068 B2 | 6/2010 | Mahon | |
| 7,825,763 B2 | 11/2010 | Dupraz et al. | |
| 7,902,812 B2 | 3/2011 | Kojovic | |
| 7,902,813 B2 | 3/2011 | Kojovic et al. | |
| 7,959,438 B2 | 6/2011 | Feine | |
| 7,969,139 B2 | 6/2011 | Ermisch et al. | |
| 8,152,800 B2 | 4/2012 | Behnke | |
| 8,179,122 B2 * | 5/2012 | Ibuki | G01R 15/181 324/117 H |
| 8,398,627 B2 | 3/2013 | Hosier | |
| 8,754,738 B2 * | 6/2014 | Kato | H01P 1/20345 29/602.1 |
| 9,956,032 B1 * | 5/2018 | Cosman | A61B 18/1477 |
| 2002/0095151 A1 * | 7/2002 | Dahla | A61B 18/148 606/41 |
| 2003/0137388 A1 * | 7/2003 | Meier | G01R 15/181 336/225 |
| 2003/0160601 A1 * | 8/2003 | Lenhard | G01R 15/185 324/117 H |
| 2003/0181898 A1 | 9/2003 | Bowers | |
| 2004/0130318 A1 * | 7/2004 | Saltsov | G01D 5/204 324/207.17 |
| 2004/0167508 A1 | 8/2004 | Wham et al. | |
| 2004/0178875 A1 | 9/2004 | Saito | |
| 2004/0257061 A1 | 12/2004 | George de Buda | |
| 2007/0063664 A1 | 3/2007 | Rhodes et al. | |
| 2008/0048646 A1 | 2/2008 | Wilkerson et al. | |
| 2008/0071260 A1 | 3/2008 | Shores | |
| 2009/0036883 A1 | 2/2009 | Behnke | |
| 2009/0243590 A1 | 10/2009 | West et al. | |
| 2010/0114090 A1 | 5/2010 | Hosier | |
| 2010/0283487 A1 | 11/2010 | Juds et al. | |
| 2011/0026180 A1 | 2/2011 | Haible et al. | |
| 2011/0043190 A1 | 2/2011 | Farr | |
| 2011/0050154 A1 | 3/2011 | Farr | |
| 2011/0062934 A1 | 3/2011 | Wolf et al. | |
| 2011/0184675 A1 | 7/2011 | White et al. | |
| 2012/0239026 A1 * | 9/2012 | Orszulak | A61B 18/1206 606/35 |
| 2013/0023870 A1 | 1/2013 | Collins | |
| 2013/0023871 A1 | 1/2013 | Collins | |
| 2013/0053840 A1 | 2/2013 | Krapohl et al. | |
| 2013/0197503 A1 | 8/2013 | Orszulak | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0345696 A1 | 12/2013 | Behnke, II et al. | |
| 2014/0002056 A1 | 1/2014 | Moul et al. | |
| 2014/0015535 A1 | 1/2014 | Lopez | |
| 2014/0025064 A1 | 1/2014 | Collins | |
| 2014/0094796 A1 | 4/2014 | Behnke, II | |
| 2014/0163431 A1 | 6/2014 | Orszulak et al. | |
| 2014/0167733 A1 | 6/2014 | Buck et al. | |
| 2014/0167740 A1 | 6/2014 | Gilbert | |
| 2014/0167786 A1 * | 6/2014 | Gutierrez | G01R 15/181 324/654 |
| 2014/0171935 A1 | 6/2014 | Digmann et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206443 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |

(56) References Cited

FOREIGN PATENT DOCUMENTS

| | | |
|---|---|---|
| EP | 694291 A1 | 1/1996 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2281521 A1 | 2/2011 |
| EP | 2407116 A1 | 1/2012 |
| EP | 2510895 A1 | 10/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 2000072027 A1 | 11/2000 |
| WO | 02/00129 | 1/2002 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2010007017 A1 | 1/2010 |

OTHER PUBLICATIONS

European Communication, dated Aug. 10, 2016, corresponding to European Application No. 15191320.9; 9 pages.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
Extended European Search Report corresponding to European Application No. 13196200.3, dated Apr. 24, 2014; 6 pages.
Extended European Search Report corresponding to European Application No. 13196199.7, dated Apr. 25, 2014; 6 pages.
European Search Report, dated Apr. 18, 2016, corresponding to European Application No. 15191279.7; 9 pages.
U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 11/242,458, filed Oct. 3, 2005, Daniel J. Becker.
European Search Report, dated Apr. 21, 2016, corresponding to European Application No. 15191320.9; 6 pages.

* cited by examiner

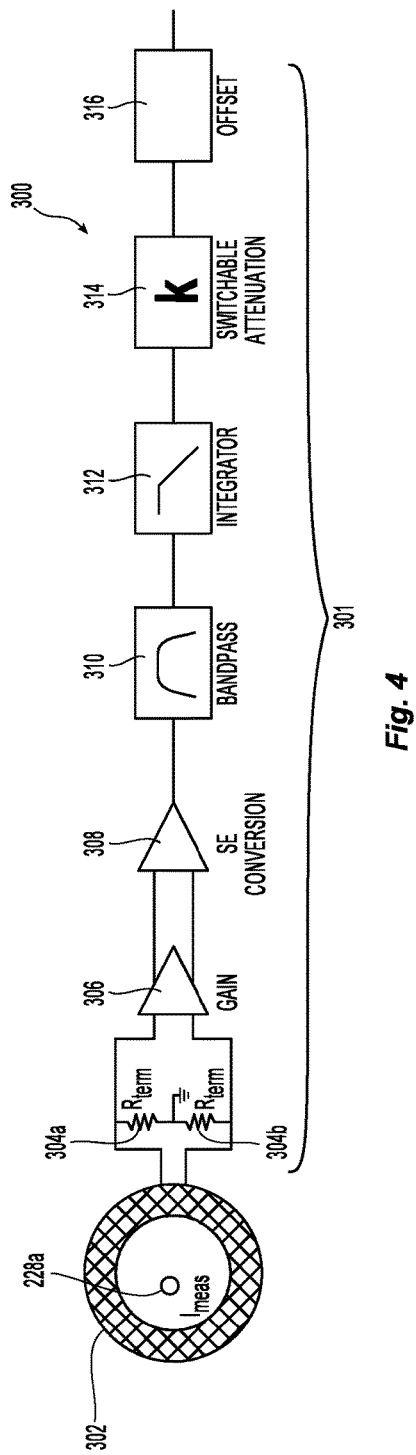
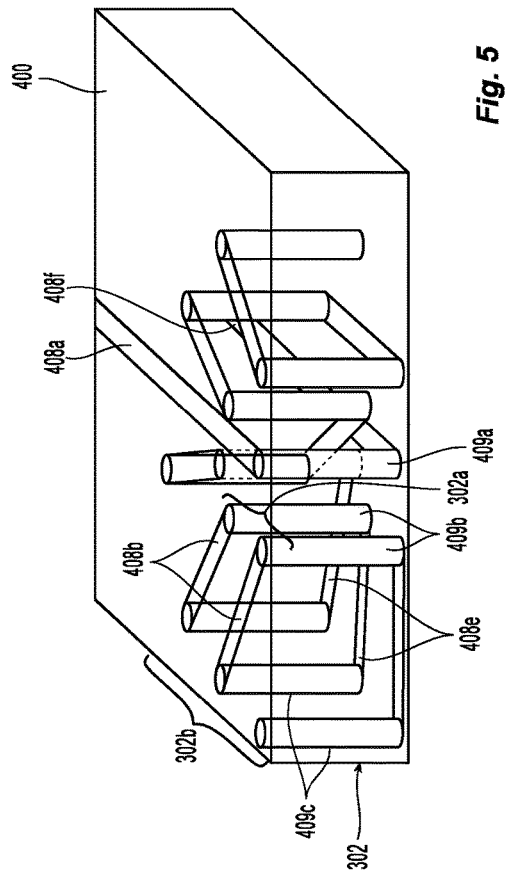

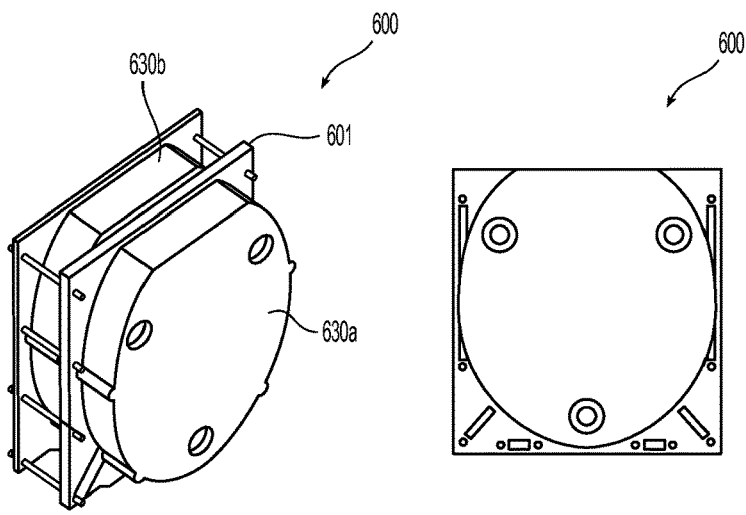
Fig. 25A
Fig. 25B
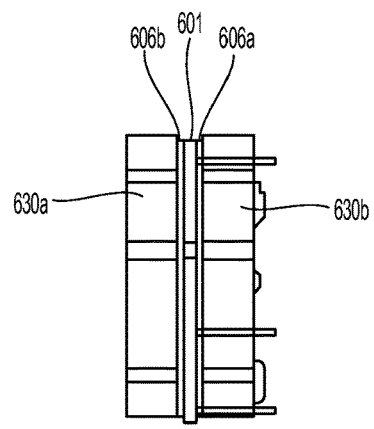
Fig. 25C
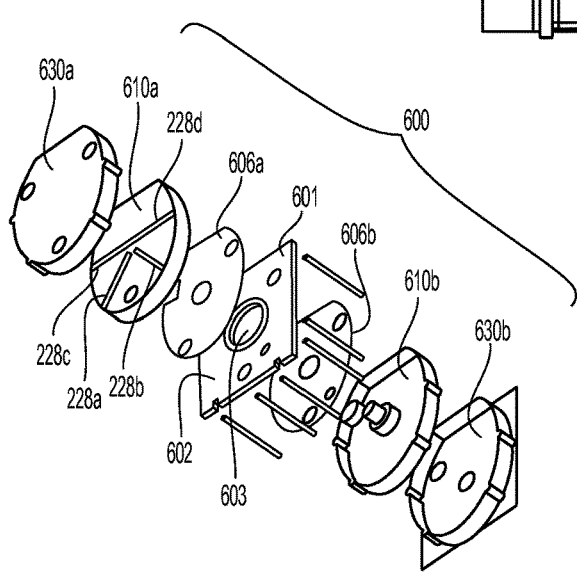
Fig. 25D

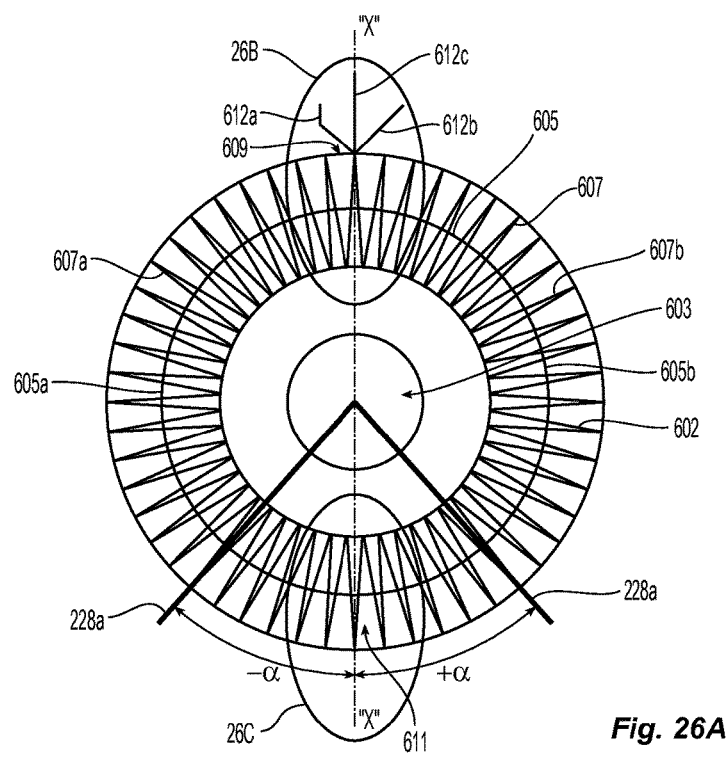
*Fig. 26A*
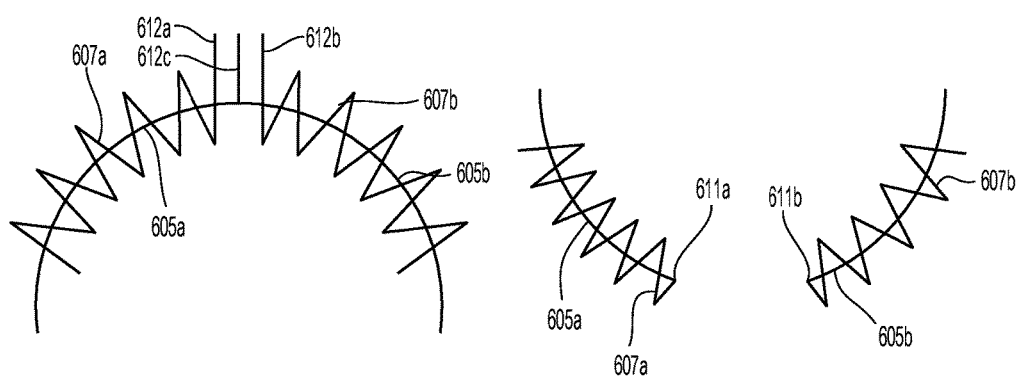
*Fig. 26B*  *Fig. 26C*

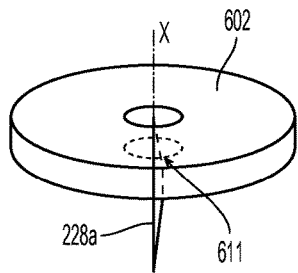
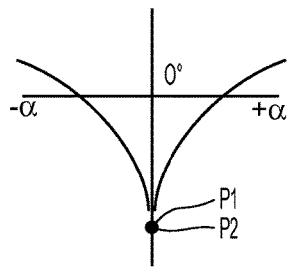
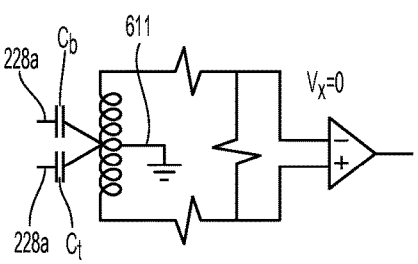
*Fig. 29A*      *Fig. 29B*      *Fig. 29C*
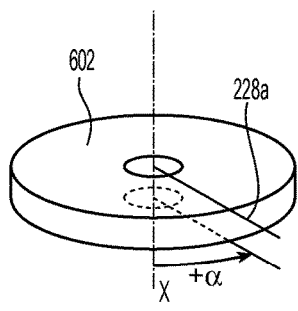
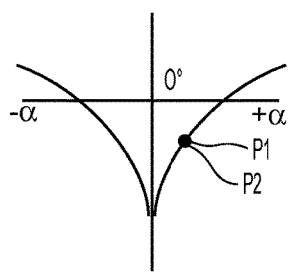
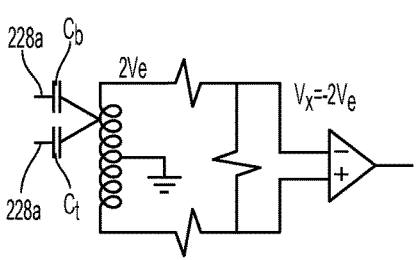
*Fig. 30A*      *Fig. 30B*      *Fig. 30C*
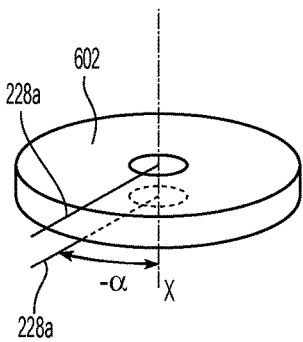
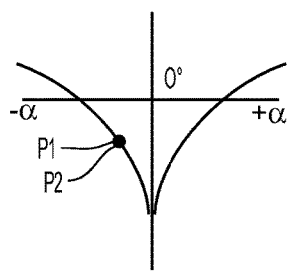
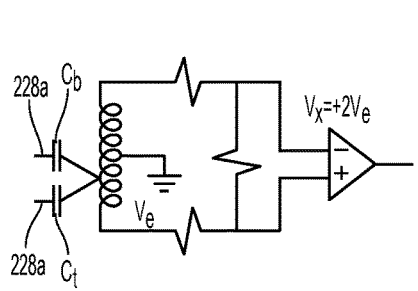
*Fig. 31A*      *Fig. 31B*      *Fig. 31C*

ELECTROSURGICAL GENERATORS AND SENSORS

CROSS-REFERENCE TO RELATED APPLICATIONS

This application is related to U.S. patent application Ser. No. 14/557,533, and U.S. patent application Ser. No. 14/557,579 both of which were filed on Dec. 2, 2014. The entire contents of each of the above applications are hereby incorporated herein by reference.

BACKGROUND

Technical Field

The present disclosure relates to an electrosurgical system and method for operating an electrosurgical generator. More particularly, the present disclosure relates to a system, apparatus, and method for measuring current in an electrosurgical generator.

Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. Electrosurgical procedures outlined above may utilize various tissue and energy parameters in a feedback-based control system. There is continual need to improve sensors that measure various tissue and energy properties utilized in the feedback-based control systems.

SUMMARY

Various embodiments of the present disclosure are described herein with reference to the drawings wherein:

According to one embodiment of the present disclosure, a sensor for sensing current is provided. The sensor includes a current sensor coil and at least one active lead and/or at least one return lead. The current sensor coil includes an outer coil and an inner coil coupled to and disposed within the outer coil. The at least one active lead and/or the at least one return lead pass through the current sensor coil opening. The current sensor coil is configured to output a differential signal indicative of a current within the at least one active lead and/or the at least one return lead.

In embodiments, the sensor may further include a conditioning circuit configured to integrate, amplify, or filter the differential signal to output a processed signal indicative of the current. The conditioning circuit may be fully-differential.

In embodiments, the sensor may further include at least one shielding member disposed over the outer coil. The current sensor coil may be disposed within a printed circuit board. The printed circuit board may include a plurality of outer conductive traces. Each outer conductive trace may be coupled to the at least one active lead. The outer conductive traces may be interconnected by at least one via through the printed circuit board. The printed circuit board may further include a top dielectric layer, a first dielectric intermediate layer, a bottom dielectric layer, and a second dielectric intermediate layer. The outer conductive traces may be disposed over the outer surfaces of the bottom and top dielectric layers. A plurality of inner and outer vias may interconnect the pluralities of top and bottom conductive traces. The shielding member may be disposed over an outer dielectric layer, which is disposed over the outer surface of at least one of the top dielectric layer or the bottom dielectric layer. The inner coil may include at least one conductive trace disposed within the outer coil and between the first and second dielectric intermediate layers of the printed circuit board. In embodiments, the shielding member may be disposed over at least one of the top dielectric layer or the bottom dielectric layer.

In embodiments, the current sensor coil may include diametrically opposed first and second ends. Each of the outer coil and the inner coil may include first and second portions. The first and second portions may be separated at the second end. The conditioning circuit may include first and second terminals coupled to the first and second portions of the outer coil, respectively. The first and second portions of the inner coil may be coupled to a third ground terminal at the first end. The first portions of the outer coil and the inner coil may be coupled to each other at the second end and the second portions of the outer coil and the inner coil may be coupled to each other at the second end.

In embodiments, the at least one active lead and/or the at least one return lead may be symmetrically disposed over the current sensor coil about an axis defined between the first and second ends. The at least one active lead and/or the at least one return lead may be disposed at a non-zero angle relative to the axis. The at least one active lead and/or the at least one return lead may be disposed transversely relative to the axis.

In another aspect of the present disclosure, another embodiment of a sensor for sensing current is provided. The sensor includes a current sensor coil and at least one active lead. The current sensor coil defines an opening therethrough and diametrically opposed first and second ends. The current sensor coil includes an outer coil and an inner coil. The outer coil includes a first semi-circular portion and a second semi-circular portion. The inner coil is disposed within the outer coil and includes a first semi-circular portion and a second semi-circular portion. The first semi-circular portions and the second semi-circular portions of the inner and outer coils are separated at the second end. The at least one active lead passes through the current sensor coil. The current sensor coil is configured to output a signal indicative of a current within the at least one active lead.

In embodiments, a conditioning circuit may be coupled to the inner and outer coils at the first end. The conditioning circuit is configured to at least one of integrate, amplify, or filter the differential signal to output a signal indicative of the current.

In embodiments, the sensor may include at least one return lead passing through the current sensor coil. The current sensor coil may be configured to output a second signal indicative of a current within the at least one return lead.

BRIEF DESCRIPTION OF THE DRAWINGS

Various embodiments of the present disclosure are described herein with reference to the drawings wherein:

FIG. 4 is a schematic diagram of a current sensor according to the present disclosure;

FIG. 5 is a partially-exposed, isometric view of a current sensor disposed within a printed circuit board according to the present disclosure;

FIG. 25A is a perspective view of a current sensor coil according to the present disclosure;

FIG. 25B is a front view of the current sensor coil of FIG. 25A according to the present disclosure;

FIG. 25C is a side view of the current sensor coil of FIG. 25A according to the present disclosure;

FIG. 25D is an exploded view of the current sensor coil of FIG. 25A according to the present disclosure;

FIG. 26A is a partially-exposed, plan view of a current sensor coil of the current sensor of FIG. 25A according to one embodiment of the present disclosure;

FIG. 26B is an enlarged area 26B of the current sensor coil of FIG. 26A according to the present disclosure;

FIG. 26C is an enlarged area 26C of the current sensor coil of FIG. 26A according to the present disclosure;

FIG. 29A is a perspective, schematic view of the current sensor coil according to another embodiment of the present disclosure;

FIG. 29B is a plot of an erroneous error signal as function of lead position of the current sensor coil of FIG. 29A as a function of an angle of leads passing therethrough according to the present disclosure;

FIG. 29C is a schematic diagram of the current sensor of FIG. 29A with parasitic capacitive coupling according to the present disclosure;

FIG. 30A is a perspective, schematic view of the current sensor coil according to another embodiment of the present disclosure;

FIG. 30B is a plot of an erroneous error signal as function of lead position of the current sensor coil of FIG. 30A as a function of an angle of leads passing therethrough according to the present disclosure;

FIG. 30C is a schematic diagram of the current sensor of FIG. 30A with parasitic capacitive coupling according to the present disclosure;

FIG. 31A is a perspective, schematic view of the current sensor coil according to another embodiment of the present disclosure;

FIG. 31B is a plot of an erroneous error signal as function of lead position of the current sensor coil of FIG. 31A as a function of an angle of leads passing therethrough according to the present disclosure;

FIG. 31C is a schematic diagram of the current sensor of FIG. 31A with parasitic capacitive coupling according to the present disclosure;

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus. In further embodiments, the generator may include a current sensor coil configured to sense current supplied to one or more electrosurgical instruments. The current sensor coil according to the present disclosure minimizes and/or eliminates, the unwanted signal that is coupled via the parasitic capacitances, which can lead to erroneous current sensor measurements. In embodiments, coupling is directed to ground through a shielding member. In further embodiments, the signal is zeroed by coupling an additional equal, but opposite voltage signal.

Figure 1:
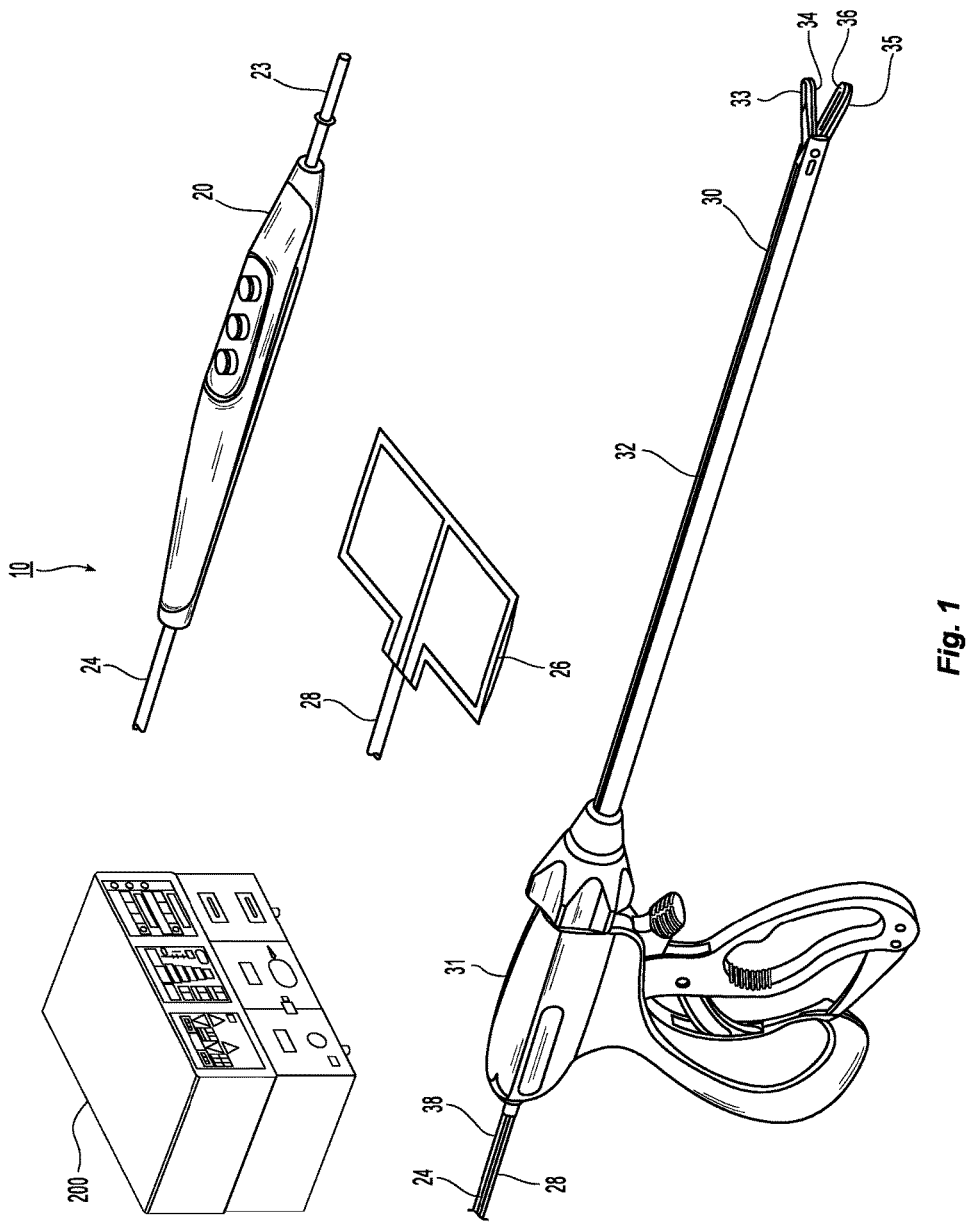
FIG. 1 is a perspective view of the components of one illustrative embodiment of an electrosurgical system according to the present disclosure.

FIG. 1 is a perspective view of the components of one illustrative embodiment of a bipolar and monopolar electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating current is supplied to the instrument 20 by a generator 200 via a supply line 24 that is connected to an active terminal 230 (FIG. 3) of the generator 200, allowing the instrument 20 to cut, coagulate, ablate and/or otherwise treat tissue. The alternating current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
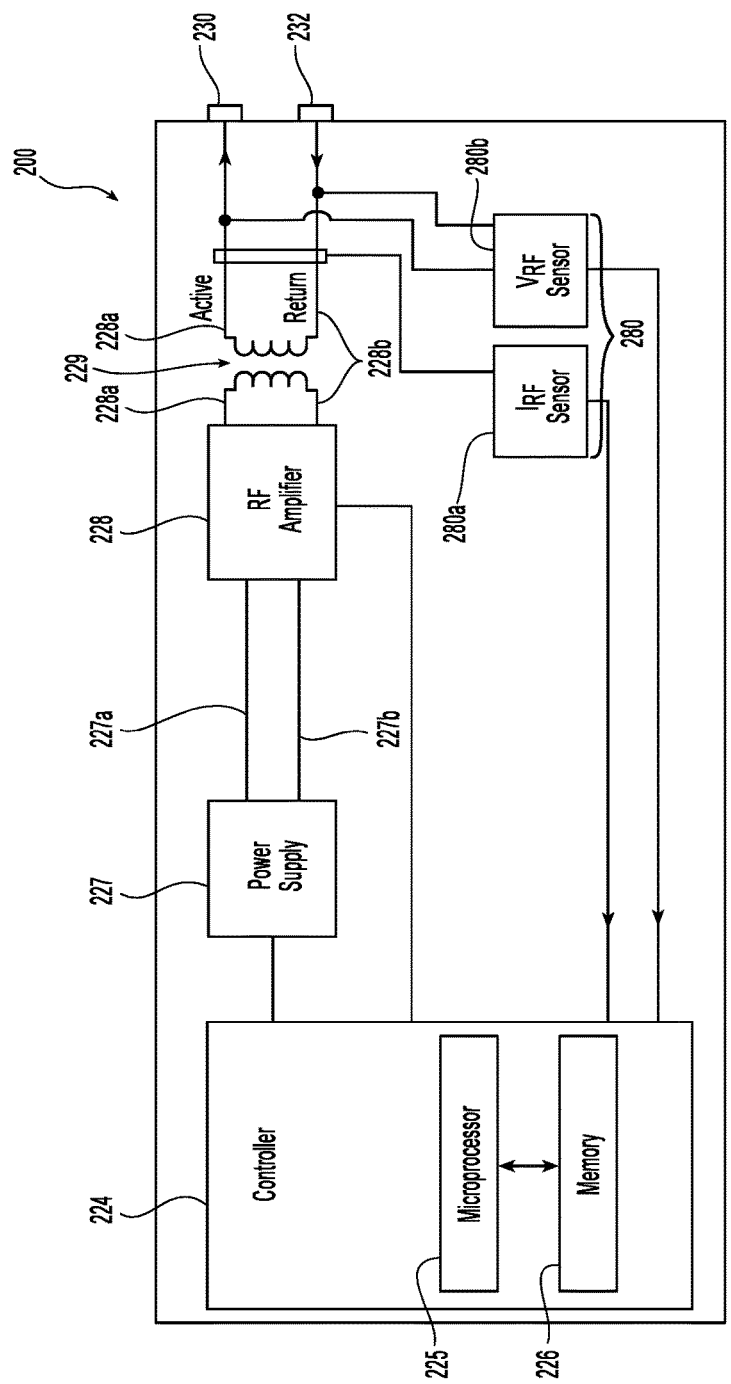
FIG. 3 is a schematic, block diagram of the embodiment of an electrosurgical generator of FIG. 2 according to the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28 coupled to the active and return terminals 230, 232, respectively (FIG. 3). The electrosurgical forceps 30 is coupled to the generator 200 at a connector having connections to the active and return terminals 230 and 232 (e.g., pins) via a plug disposed at the end of the cable 38, wherein the plug includes contacts from the supply and return lines 24, 28 as described in more detail below.

Figure 2:
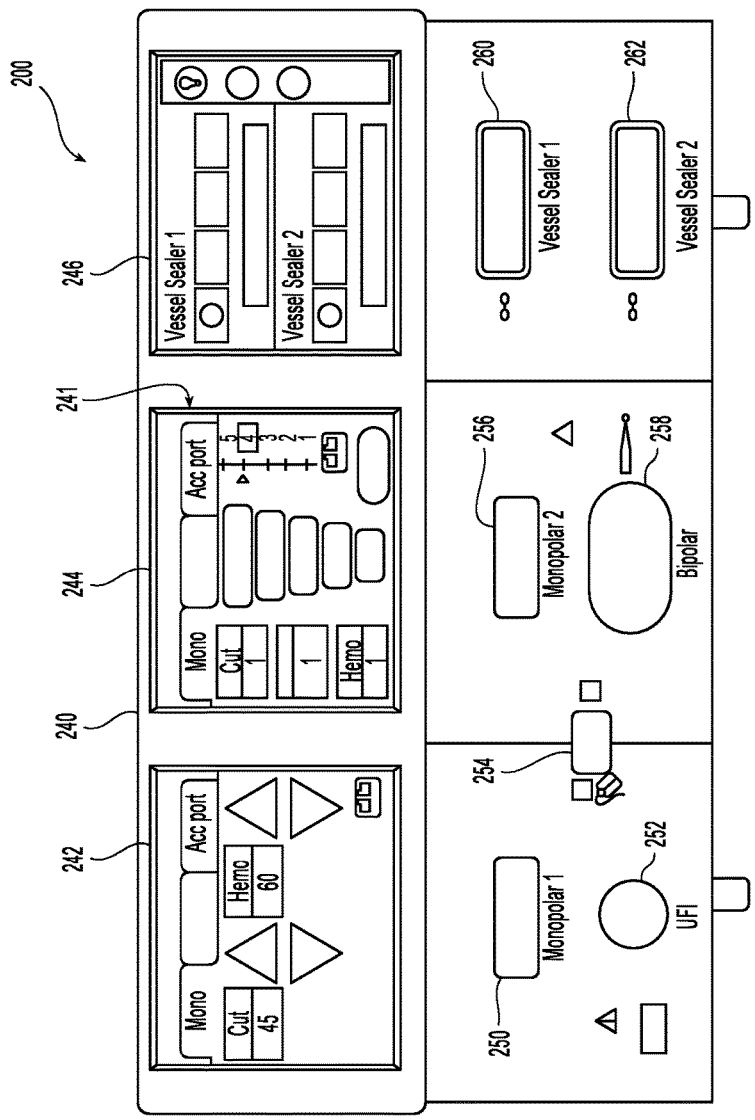
FIG. 2 is a front view of one embodiment of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250, 252, 254, 256, 258, 260, 262 to accommodate various types of electrosurgical instruments (e.g., electrosurgical forceps 30, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connectors 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 30, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 20) and connector 252 is configured to couple to a foot switch (not shown). The foot switch provides for additional inputs (e.g., replicating inputs of the generator 200). Connector 254 is configured to couple to electrode pad 26. Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 30 that may be plugged into the connectors 260 and 262. The generator 200 outputs energy through the connectors 260 and 262 suitable for sealing tissue grasped by the forceps 30. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 224 of generator 200 (FIG. 3) where the setting may be saved in memory 226. In embodiments, the intensity setting may be a number scale, such as for example, from one to ten or one to five. In embodiments, the intensity setting may be associated with an output curve of the generator 200. The intensity settings may be specific for each forceps 30 being utilized, such that various instruments provide the user with a specific intensity scale corresponding to the forceps 30.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The current is returned thereto via the return terminal 232 as energy is dissipated into the tissue. The active and return terminals 230 and 232 are coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively. Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the plurality of active leads 228a and/or plurality of return leads 228b and provides measurements of the RF current supplied by the RF amplifier 228. The RF voltage sensor 280b is coupled to the active and return terminals 230 and 232 and provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 20 and/or forceps 30. The controller 224 utilizes the input signals to adjust the power output by the generator 200 and/or performs other control functions thereon.

Transformers are conventionally used as current and voltage sensors as they provide a required patient isolation. However, the gain that transformers provide fluctuates due to temperature, signal amplitude, etc. This makes accurate readings difficult with respect to the phase and gain-bandwidth of the sensor signals. As a result, the signals need to be post-processed to arrive at accurate representations. The present disclosure provides for novel current sensor 280a which overcome the problems of conventional sensors.

FIG. 4 shows an RF current sensor 300, which includes a conditioning circuit 301 and a current sensor coil 302. As used herein, the term "current sensor coil" refers to an electrical device for measuring alternating current (e.g., RF current) and includes an outer conductor coil (e.g., toroid) that acts as an active conductor wrapped around an inner conductor, a so-called "Bucking coil" that acts as a return conductor and a lead 228a carrying the current passing through an opening 303 (FIG. 6) in the coil 302. The coil 302 may have any suitable shape such as helical, toroidal, etc. In embodiments, the coil may have a polygonal cross-section. The current sensor coil 302 may include a low permeability core (e.g., air core) and provides a voltage output having a time-derivative of the current being measured to a conditioning circuit that integrates the output to provide a voltage signal indicative of the current. In embodiments, the current sensor coil 302 may be implemented on a printed circuit board and may include an opening so that the current sensor coil 302 may be wrapped about the conductor carrying the current to be measured. In further embodiments, the current sensor coil 302 may also be implemented using wire and may be wound around a toroidal magnetic core.

The current sensor coil 302 is coupled to conditioning circuit 301 having a resistor network 304, which includes resistors 304a and 304b. In embodiments, the conditioning circuit 301 may be implemented as any integrator (e.g., logic processor) or differential amplifier. The resistor network 304 removes resonance of the coil 302 at its resonant frequency. As described in further details below with respect to FIGS. 5-9, the current sensor coil 302 is disposed about one or more active leads 228a and the coil 302 is configured to measure the current passing therethrough as a sensor signal. The sensor signal from the coil 302 is then supplied to an optional gain amplifier 306 which increases the amplitude of the sensor signal and buffers the coil 302. The gain amplifier 306 or the coil 302, if the gain amplifier 306 is not used, is also coupled to an amplifier 308, which is in turn, coupled to a bandpass filter 310. The amplifier 308 is a differential-to-single-ended converter whose function is to convert the differential signal from the coil 302 to a single-ended signal. The amplifier 308 may have a monolithic configuration that provides improved common mode rejection.

The bandpass filter 310 removes higher and lower frequency components of the sensor signal which is then transmitted to an integrator 312. Since the voltage that is induced in the current sensor coil 302 is proportional to the rate of change of current that is flowing through the active lead 228a, the integrator 312 is utilized to provide an output sensor signal that is proportional to the current.

In embodiments, the integrator 312 may be coupled to a switchable attenuation circuit 314, which may include one or more actively switched components. The attenuation circuit 314 may then be coupled to additional components such as an offset circuit 316, analog-digital converters, and the like prior to supplying the signal to the controller 224.

FIGS. 5-9 show the current sensor coil 302 according to the present disclosure. The coil 302 has a substantially circular shape having an opening 303 (FIG. 6) defined therethrough. The active lead 228a is disposed through the opening 303 of the coil 302, allowing the coil 302 to measure the current flow through the active lead 228a. If the return lead 228b is also being measured, additional traces may be used to provide for passage through the opening 303 of the current sensor coil 302 as described in detail below with respect to FIGS. 17-33.

Figure 6:
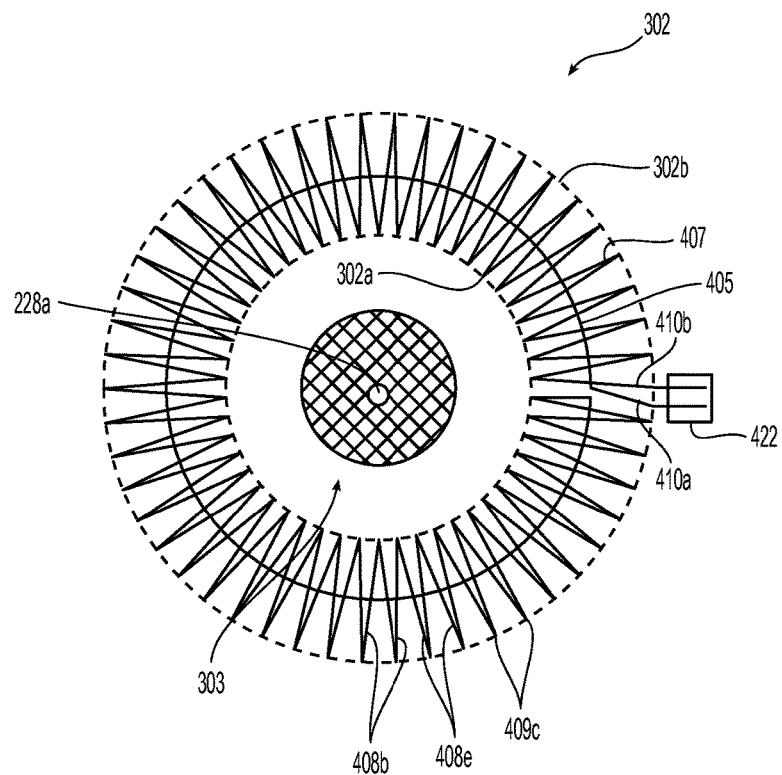
FIG. 6 is a partially-exposed, plan view of a current sensor coil of FIG. 5 according to the present disclosure.

As shown in FIGS. 5 and 6, the coil 302 has a substantially toroidal shape and is formed on a printed circuit board (PCB) 400 and includes an inner circumferential region 302a and an outer circumferential region 302b. The coil 302 includes forming an inner portion ("Bucking coil") 405 of the coil 302 and an outer coil 407. In embodiments, the coil 302 may have any other suitable shape (e.g., having a polygonal cross-section) with the outer coil 407 wrapped about the inner coil 405 and defining an opening through the coil 302. In embodiments, the coil 302 may be a coil-wrapped phenolic toroid having a low permeability ($\mu_0$).

In embodiments, where only one of the active leads 228a is used, the magnetic field is reflective of the current Ip passing only through the active lead 228a. The outer coil 407 detects the magnetic field in either embodiment and produces a first voltage corresponding to the first magnetic field. The outer coil 407 also may detect a second unwanted magnetic field and produces a second voltage corresponding to the second magnetic field. The second magnetic field is orthogonal to the first magnetic field and is not related to the sensed current. The inner coil 405 senses the second magnetic field and produces a third voltage proportional to the second magnetic field. The second voltage and third voltage produced have approximately the same magnitude such that they cancel each other. In embodiments where the plurality of active leads 228a and/or plurality of return leads 228b are disposed together, the current flowing through the active leads 228a and return leads 228b produce a net first magnetic field proportional to the sensed current Is.

Figure 8:
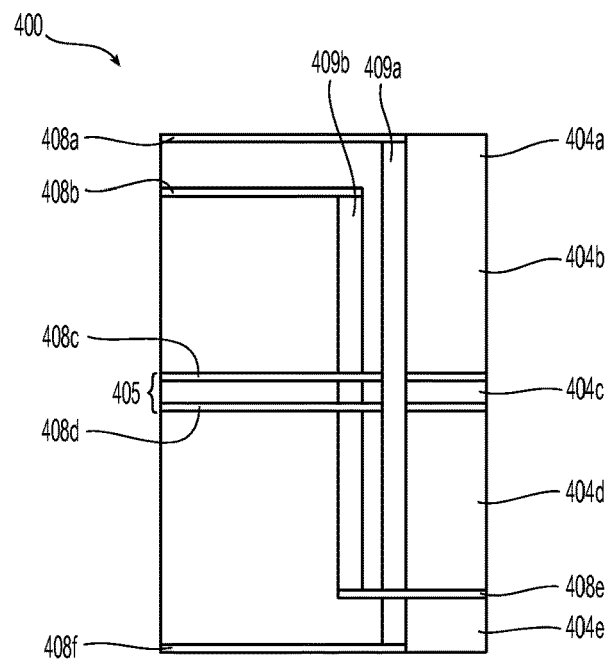
FIG. 8 is a side, partial cross-sectional view of the printed circuit board of FIG. 5 according to the present disclosure.
Figure 9:
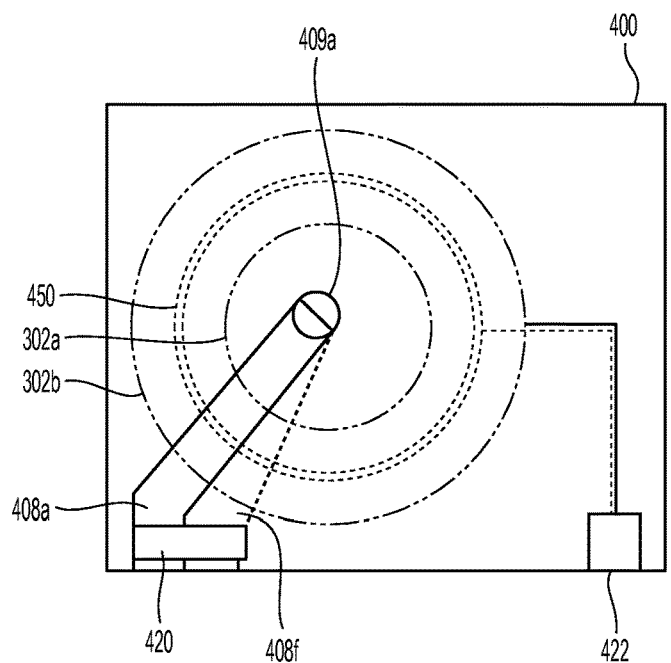
FIG. 9 is a plan view of the printed circuit board of FIG. 5 according to the present disclosure.

The PCB 400 may be a multilayer PCB formed from any suitable dielectric material, including, but not limited to composite materials composed of woven fiberglass cloth with an epoxy resin binder such as FR-4 grade as designated by National Electrical Manufacturers Association. As shown in FIG. 8, the PCB 400 includes a first or top layer 404a and a bottom layer 404e. For simplicity FIG. 5, FIG. 6, FIG. 8, and FIG. 9 will show only the active lead 230. It will be understood that in every case a plurality of active leads and/or a plurality of return leads may be used. The active lead 228a is coupled to conductive traces 408a and 408f, respectively, which are disposed over the top and bottom layers 404a and 404e as shown in FIGS. 8 and 9. The active lead 228a may be coupled to a patient side connector 420 disposed on the PCB 400 as shown in FIG. 9. The traces 408a and 408f are interconnected through the opening 303 (FIG. 6) using one or more vias 409a, which pass through the entire PCB 400 (e.g., layers 404a-404e).

The outer coil 407 includes a top trace 408b disposed between the top layer 404a and an intermediate layer 404b of the PCB 400. The outer coil 407 also includes a bottom trace 408e disposed between the bottom layer 404e and an intermediate layer 404d of the PCB 400. The traces 408b and 408e are interconnected by a plurality of inner vias 409b and outer vias 409c. The layers 404a and 404e insulate the coil 302 (e.g., outer coil 407) conductive traces 408a and 408f and provide an isolation barrier between the patient and the generator 200.

Figure 7:
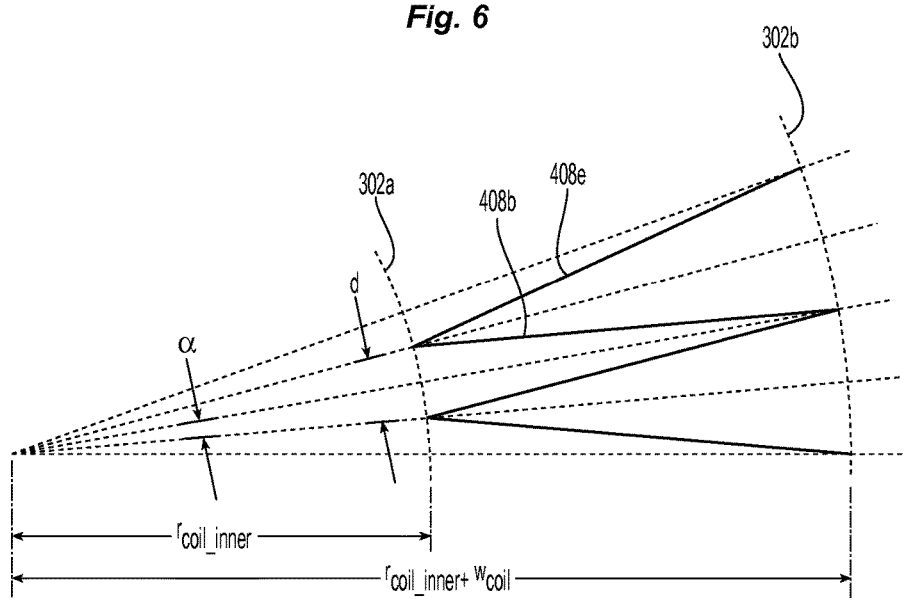
FIG. 7 is an enlarged schematic view of the current sensor coil of FIG. 6 according to the present disclosure.

As shown in FIGS. 5-7, the inner vias 409b are arranged to form the inner circumferential region 302a of the coil 302 and the outer vias 409c form the outer circumferential region 302b of the coil 302. The inner and outer vias 409b and 409c pass through the layers 404b, 404c, and 404d. The inner vias 409b and outer vias 409c may be disposed in a concentric configuration. In a non-staggered configuration, corresponding inner and outer vias 409b and 409c lie along same rays. In a staggered configuration, the inner and outer vias 409b and 409c lie along alternating rays "r" as shown in FIGS. 5-7. The rays "r" are disposed at and an angle "α" relative to each other and the inner vias 409b are separated by a distance "d." Each of the inner vias 409b is connected to two neighboring outer vias 409c through traces 408b and 408e and vice versa. The interconnection of the vias 409b and 409c with the traces 408b and 408e forms a plurality of loops, which in turn, form the outer coil 407 as shown in FIG. 5.

The outer coil 407 may include any suitable number of turns, in embodiments from about 50 turns to about 100 turns. The maximum number of turns depends on the radius of the inner circumferential region 302a, via aspect ratio, thickness of the outer coil traces 407 and/or PCB 400, and spacing between the turns based on the limits of manufacturability of the PCB material (e.g., trace to trace, trace to via, via annular pad dimension, anything that may limit the placement of the conductors on the PCB).

With reference to FIGS. 6 and 8, the inner coil 405 is disposed within the outer coil 407 and also has a substantially circular shape. The inner coil 405 may include an upper trace 408c and a bottom trace 408d. The traces 408c and 408d are disposed over a dielectric layer 404c, such that the traces 408c and 408d are insulated from each other. The traces 408c and 408d may be electrically coupled to each other. In embodiments, the inner coil 405 may be formed from a single trace.

As shown in FIGS. 6 and 9, the coil 302 is coupled to the conditioning circuit 301 at a side connector 422, which may also be disposed on the PCB 400. The coil 302 includes a first terminal 410a coupled to the inner coil 405 and a second terminal 410b coupled to the outer coil 407. In particular, the outer coil 407 is disposed over the inner coil 405 and is coupled thereto. Thus, two terminals 410a and 410b are disposed at one end of the coil 302. The interconnection between the inner coil 405 and the outer coil 407 as well as the connection to the terminals 410a and 410b may be made through the vias 409b and 409c.

The controller 224 is provided to sensor signals from the sensor 300, which are then utilized to determine the current. Various formulas may be utilized by the controller 224 to determine the current. The voltage produced by the coil 302 may be calculated using the formula (I):

$$V_{OUT} = \frac{-A_{LOOP}N_{LOOPS}}{2\pi R_{COIL}} \mu_0 \frac{dI}{dt} \quad (I)$$

In formula (I), A is the area of the turn (e.g., loop) formed by the vias 409b and 409c with the traces 408b and 408e, N is the number of turns, R is the major radius of the coil 302, $\mu_0$ is the magnetic constant, dI/dt is the rate of change of the current being measured by the coil 302.

Inductance and capacitance of the coil may be calculated using the formulae (II)-(IV), respectively. Capacitance of the coil 302 is used to determine self-resonance and may be calculated using parallel-wire model formulae, namely, capacitances of inner and outer vias 409b and 409c and traces 408b and 408e.

$$L_{Coil} = \frac{\mu_0 \cdot N_{Turns}^2 \cdot l_{coil}}{2\pi} \ln\left(\frac{r_{coil\_inner} + w_{coil}}{r_{coil\_inner}}\right) \quad (II)$$

$$C_{Coil} = N_{Turns} \cdot \left(2 \cdot C_{trace-trace} + C_{via-inner} + C_{via-outer}\right) \quad (III)$$

$$C_{\parallel} = \frac{\pi \cdot \varepsilon_0 \cdot \varepsilon_r \cdot l_{trace/via}}{\ln\left(\frac{d_{between\_trace/via}}{2 \cdot r_{via/trace}} + \sqrt{\frac{d_{between\_trace/via}^2}{r_{via/trace}^2} - 1}\right)} \quad (IV)$$

In formulae (II)-(IV), in addition to the variable and constants utilized in formula (I), t is thickness (e.g., distance between conductive traces 408b and 408e), r is radius, w is the radial distance between inner and outer circumferential regions 302a and 302b, Rcoil_inner is the radial distance to the inner circumferential region 302a, l is length, $\varepsilon_0$ is vacuum permittivity constant, and $\varepsilon_r$ is the relative dielectric constant of the PCB.

With reference to FIGS. 4 and 10-15, components of conditioning circuit 301 of the sensor 300 is shown. Since the coil 302 provides a differentiating response, the output must be integrated to provide the actual response through the conditioning circuit 301 of the sensor 300. The output of the coil 302 is integrated to produce a signal that is proportional to the current in the active lead 228a. The conditioning circuit 301 provides integration with the integrator 312. This allows for easy adjustability of the sensor gain, utilization in the control loop and processing by an analog-digital converter. Gain may be set by adjusting the frequency setpoint of the integrator 312. The setpoint may be achieved by selection of hardware component values (e.g., discrete resistor or capacitor substitution), selection of software values (e.g., digital or analog potentiometers or adjustable capacitors), including programmable gain amplifiers as described in detail below, or combinations thereof.

Figure 10:
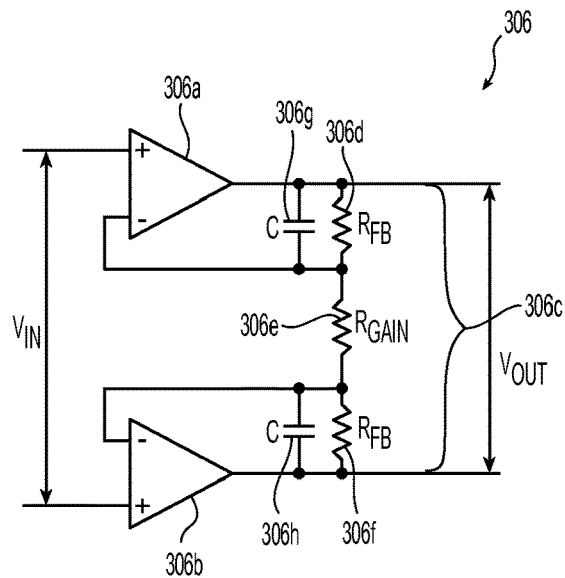
FIG. 10 is a schematic circuit diagram of a gain amplifier according to the present disclosure.

The gain amplifier 306 of the conditioning circuit 301 is shown in FIG. 10 and includes a pair of operational amplifiers 306a and 306b configured to provide differential gain without adding to the common-mode gain. The sensor signal from the coil 302 is provided to the positive terminals of the amplifiers 306a and 306b. The outputs of the amplifiers 306a are interconnected by a gain setting voltage divider network 306c including three resistors 306d, 306e, 306f. Terminal resistors 306d and 306f are coupled in parallel with capacitors 306g and 306h, respectively. The signal from the parallel circuits is coupled to the negative terminals of the amplifiers 306a and 306b, which provide closed-loop feedback thereto. Capacitors 306g and 306h provide amplifier stabilization and may also provide for the integration of the signal.

Figure 11:
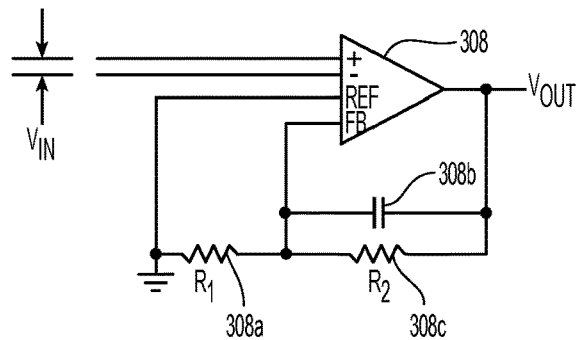
FIG. 11 is a schematic circuit diagram of a differential to single-ended amplifier according to the present disclosure.
Figure 12:
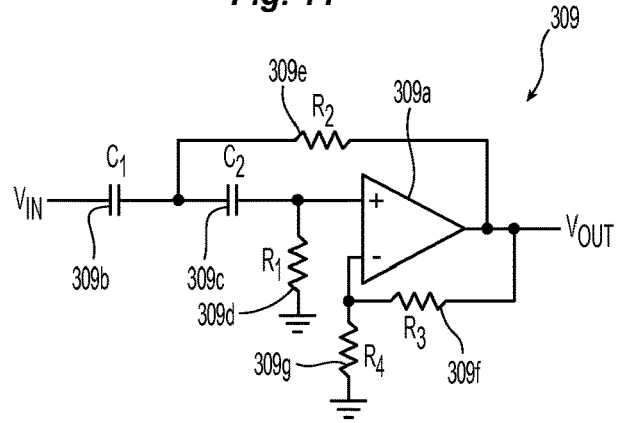
FIG. 12 is a schematic circuit diagram of a high-pass filter according to the present disclosure.
Figure 13:
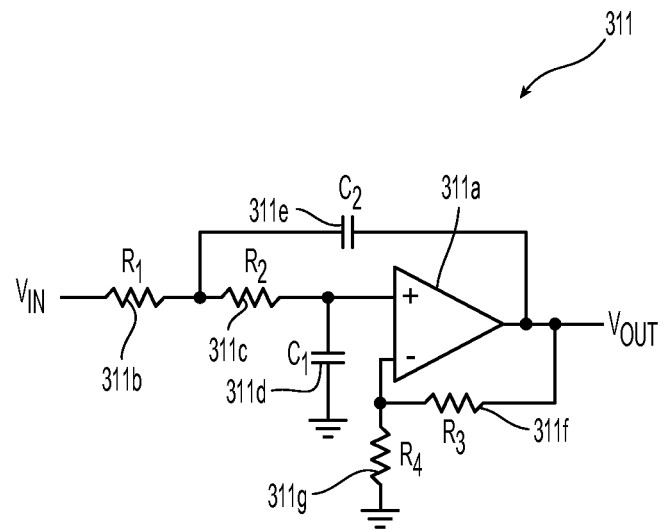
FIG. 13 is a schematic circuit diagram of a low-pass filter according to the present disclosure.
Figure 14:
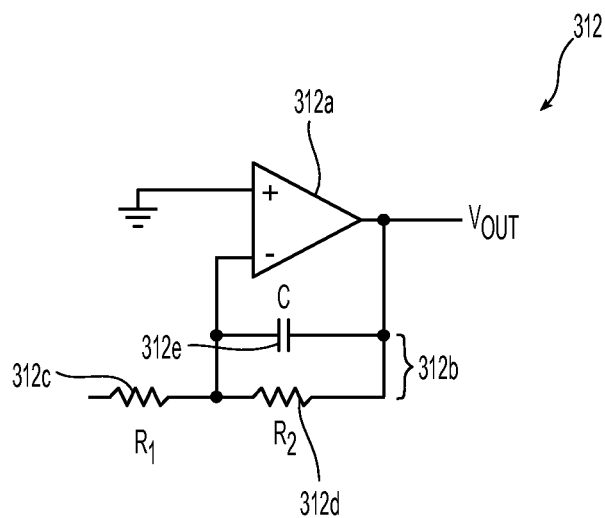
FIG. 14 is a schematic circuit diagram of an integrator according to the present disclosure.

The output of each of the operational amplifiers 306a and 306b is provided to the differential to single-ended amplifier 308, which is shown in FIG. 11. In particular, the output of the amplifiers 306a and 306b is supplied to the positive and negative inputs of the amplifier 308. The amplifier 308 combines the output of the amplifiers 306a and 306b to provide a single output to the bandpass filter 310. The amplifier 308 includes a closed feedback circuit having a reference signal connected to ground including a resistor 308a, which is connected in series with a capacitor 308b that is coupled in parallel with a resistor 308c. The bandpass filter 310 includes a high-pass filter 309 and a low-pass filter 311 as shown in FIGS. 12 and 13, respectively. In embodiments, the output from the amplifier 308 may be passed through the high-pass filter 309 before being passed through the low-pass filter 311, or vice versa.

The high-pass filter 309 is configured to pass high frequencies and attenuate lower frequencies. The high-pass filter 309 includes an operational amplifier 309a. The output from the amplifier 308 is provided to the input of the amplifier 309a through a first capacitor 309b coupled in series with a second capacitor 309c and a first resistor 309d and a second resistor 309e. The negative input of the amplifier 309a is provided by a feedback loop from a third resistor 309f coupled in series with a grounded fourth resistor 309g.

The low-pass filter 311 is configured to pass low frequencies and attenuates higher frequencies. The low-pass filter 311 includes an operational amplifier 311a. The input from the high-pass filter 309 is provided to the input of the amplifier 311a through a first resistor 311b coupled in series with a second resistor 311c and a first capacitor 311d and a second capacitor 311e. The negative input of the amplifier 311a is provided by a feedback loop from a third resistor 311f coupled in series with a grounded fourth resistor 311g.

Since the voltage that is induced in the current sensor coil 302 is proportional to the rate of change of current that is flowing through the active lead 228a, the integrator 312 is utilized to provide an output signal that is proportional to the sensed current. In embodiments, a leaky integrator may be used. As used herein the term "leaky integrator" refers to an integrator having a low-pass filter as described in further detail below with respect to FIG. 14. The integrator 312 includes an amplifier 312a with a positive input thereof coupled to a ground. The input from the bandpass filter 310 is fed through a low-pass filter 312b, which includes a first resistor 312c coupled in series with a second resistor 312d that is coupled in parallel with a capacitor 312e. The second resistor 312d and the capacitor 312e are also coupled to the output of the amplifier 312a thereby providing a closed loop feedback thereto. The input signal is then fed to the negative input of the amplifier 312a.

The integrator 312 provides a negative slope of voltage gain verses frequency. This compensates, or flattens the opposite slope of the signal coming from the coil 302. Further, the integrator 312 has extremely high DC gain. The frequency band of interest for the generator 200 is well above DC. The integrator gain would create problems if a DC offset were present at its input. The high-pass portion of the band-pass filter 310 reduces the low frequency components and reduces any DC offset, which mitigates issues caused by the integrator's amplification of these components.

Figure 15:
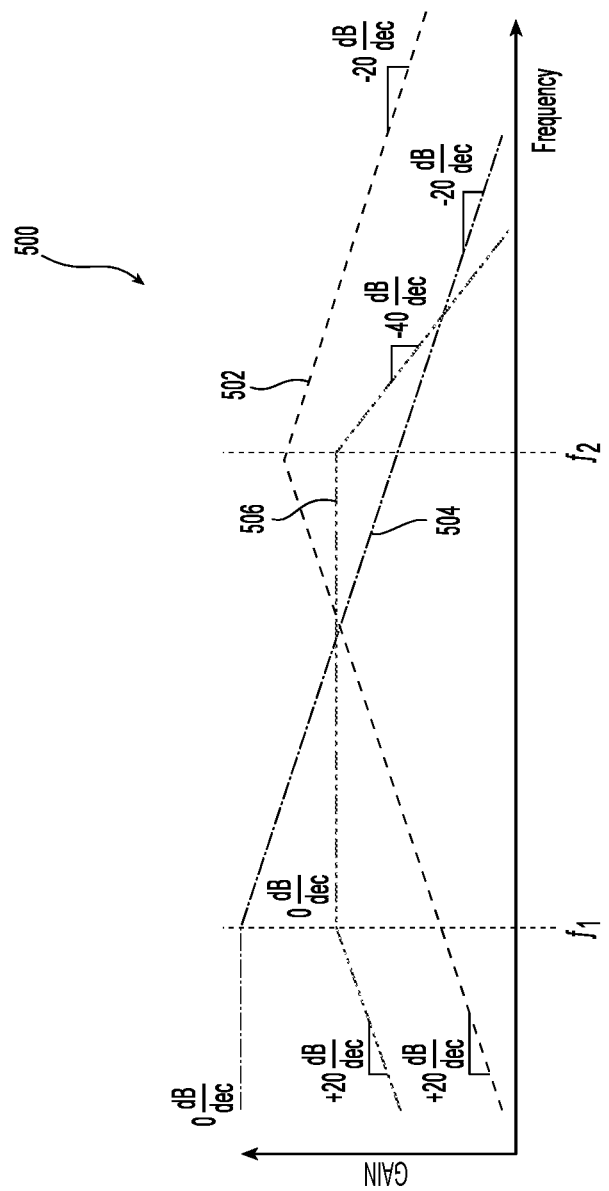
FIG. 15 is a plot of individual and combined gain response of the current sensor coil of FIG. 4 and the integrator shown in FIG. 14 according to the present disclosure.

FIG. 15 shows a graph 500 illustrating individual gain response of the coil 302, the integrator 312, and the combined response of the coil 302 and the integrator 312. The graph 500 shows the overall response of the coil 302 as a plot 502, the response of the integrator 312 as a plot 504, and the combined response of the coil 302 and the integrator 312 of the sensor 300 as a plot 506, which is a combination of the plots 502 and 504. Frequency, f1, is determined by the response of the integrator 312 and frequency, f2, is determined by the resonant frequency of the coil 302.

Figure 16:
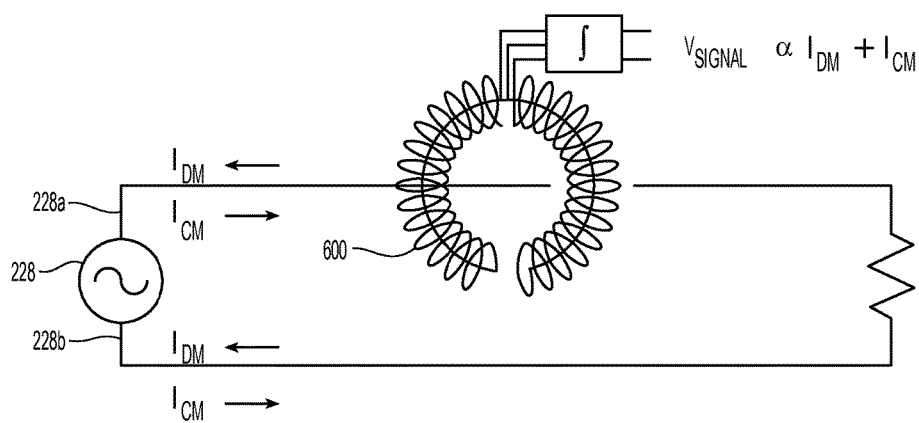
FIG. 16 is a schematic diagram of the current sensor coil of FIG. 4 according to the present disclosure.
Figure 17:
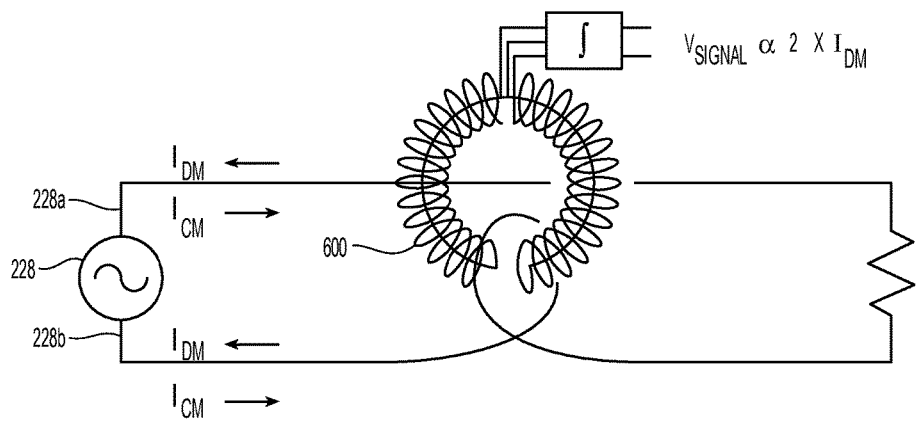
FIG. 17 is a schematic diagram of a differential-mode current sensor coil according to the present disclosure.

With reference to FIGS. 16 and 17, the active lead 228a carries both common-mode (CM) and differential-mode (DM) current. For the purpose of measuring energy delivered to the patient, DM current can provide useful data. Thus, having a system and method of separating the DM current from the CM current in a conductor would then allow for more accurate sensors. In a single-conductor Rogowski coil, the CM current and DM current are indistinguishable from one another.

With continued reference to FIG. 17, by adding a second conductor, namely, the return lead 228b, and appropriately orienting the return lead 228b through differential-mode RF current sensor 600 a signal as a function of the DM current. The relationship between the measured current and the sensor signal $V_{signal}$ depends on the core being used in the RF current sensor.

As illustrated in FIG. 17, the CM currents on the active lead 228a and return lead 228b pass through the center of the current sensor 600, but in opposite directions. The flux produced by CM currents cancel each other out, and the current sensor 600 produces zero signal in proportion to the CM current. The DM currents pass through the current sensor 600 in the same direction due to the routing of the active lead 228a and return lead 228b, namely, looping of the return lead 228b. The flux produced by DM currents are additive, and the current sensor 600 produces a signal that is based on the sum of (e.g., twice of) the DM current. If an iron or ferrite core is being used, then $V_{signal}$ is proportional to the DM current, thus in FIG. 16, $V_{signal}$ is proportional to the sum of CM and DM currents and in FIG. 17 $V_{signal}$ is proportional to the sum of only the DM currents. If an air core is being used, then $V_{signal}$ is proportional to time rate of change of $V_{signal}$, thus in FIG. 16, $V_{signal}$ is proportional to a derivative of the sum of CM and DM currents and in FIG. 17 $V_{signal}$ is proportional to the sum of time derivative of only the DM currents. Although the above-described embodiment is related to a Rogowski coil as a current sensor, the disclosed orientation of the active and return leads may be applied to any type of a current-sense transformer.

Figure 18:
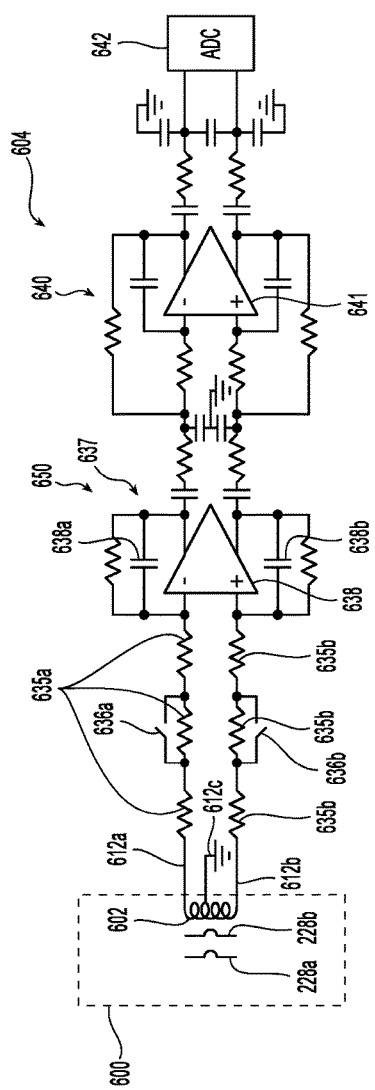
FIG. 18 shows another embodiment of a current sensor and conditioning circuit according to the present disclosure.

FIG. 18 shows a current sensor assembly 604 including the differential-mode RF current sensor 600 and a fully differential condition circuit 650 according to the present disclosure. The current sensor 600 includes a current sensor coil 602 and is shown schematically in FIG. 19. The current sensor 600 is configured to measure individual first and second currents of active and return leads 228a and 228b or a net current. Current transformers are configured to measure either common-mode current or differential-mode current flow. In a typical application using power electronics, such as an inverter for generating alternating current, complex currents flow which have both differential and common-mode components which make up the totality of the flowing current.

Figure 19:
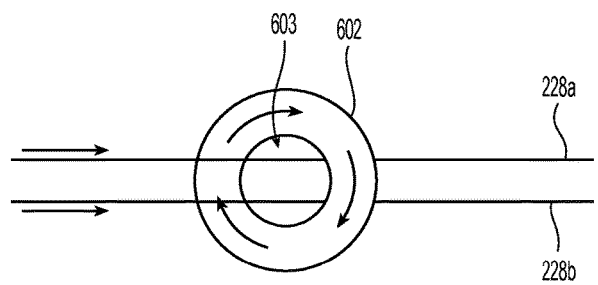
FIG. 19 is a schematic diagram of the differential-mode current sensor coil of FIG. 17 according to the present disclosure.
Figure 33:
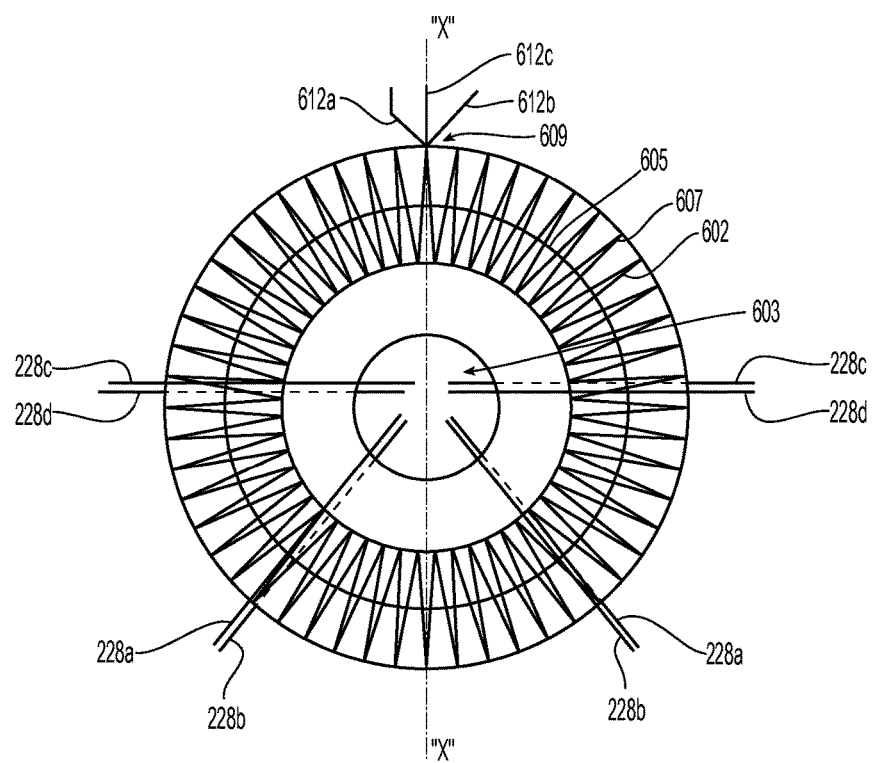
FIG. 33 is a partially-exposed, plan view of a current sensor coil of the current sensor according to a further embodiment of the present disclosure.

The current flowing through each of the leads 228a and 228b generates a corresponding magnetic field within the current sensor 600. The net magnetic field then affects the current sensor 600, which detects the differential-mode current. The embodiment of the current sensor coil 602 of FIG. 19 is configured as a differential-mode current sensor since it allows for use with multiple active and return leads 228a, 228b and 228c, 228d (FIG. 33).

The current sensor 600 and the conditioning circuit 650 provide a completely differential signal, which provides better noise immunity. First and second terminals 612a and 612b of the current sensor coil 602 are coupled to the conditioning circuit 650. Current sensor coil 602 also includes a third terminal 612c as described in further detail below with respect to FIG. 26A.

Each of the first and second terminals 612a, 612b is coupled to a differential integrator 637, which includes a plurality of resistors 635a, 635b. The differential integrator 637 compensates for the derivative nature of the sensor signal from the current sensor coil 602 as described above with respect to the current sensor coil 302. One or more of the resistors 635a, 635b may be coupled to differential gain switches (e.g., MOSFETs, analog switches, relays etc.) 636a, 636b, respectively. The switches 636a, 636b are configured to change the value of the resistors 635a, 635b, respectively, to adjust the gain of the conditioning circuit 650.

The resistors 635a, 635b are coupled to input terminals of an amplifier 638. The differential integrator 637 also includes capacitors 638a, 638b coupled to the amplifier 638. The differential integrator 637 is, in turn, coupled to an active bandpass filter 640, which also includes an amplifier 641 and associated circuit components. The bandpass filter 640 is then coupled to an analog-to-digital converter 642, which then transmits the converted digital signal to the controller 224.

Figure 20:
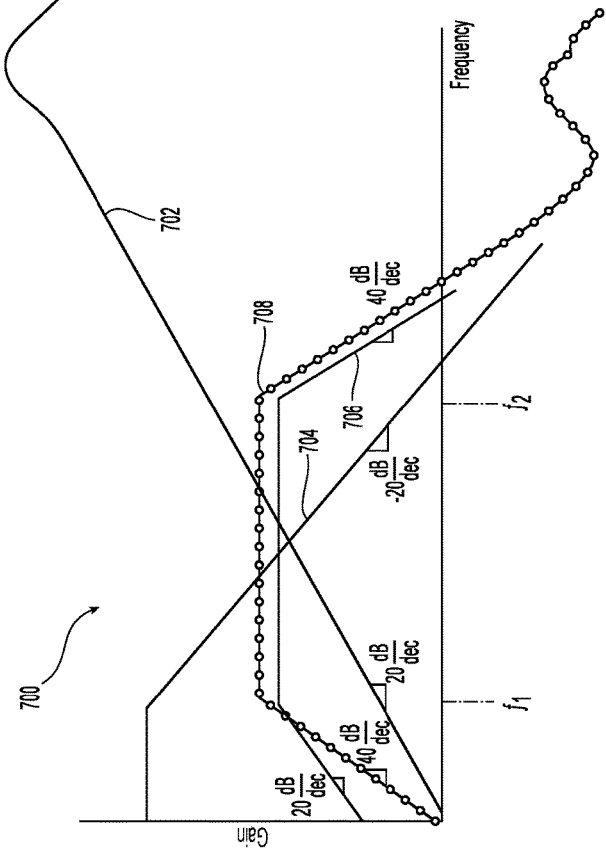
FIG. 20 is a plot of individual and combined gain response of a current sensor coil, an integrator, a bandpass filter shown in FIG. 18 according to the present disclosure.

FIG. 20 is a graph 700 of a gain response of the current sensor assembly 604 of FIG. 18 according to the present disclosure. The graph 700 shows individual and combined gain responses of the current sensor coil 602, differential integrator 637, and the bandpass filter 640. The graph 700 shows the overall response of the current sensor coil 602 as a plot 702, the response of the differential integrator 637 as a plot 704, and the response of the bandpass filter 640 as a plot 706. The graph 700 also shows the combined response of the current sensor coil 602, differential integrator 637, and the bandpass filter 640 as a plot 708, which is a combination of the plots 702, 704, and 706. Frequency, f1, is determined by the response of the differential integrator 637 and the bandpass filter 640, and frequency, f2, is determined by the bandpass filter 640.

In certain situations, the RF energy passing through the leads 228a and 228b may have relatively high voltage but low current. Undesired voltage signal from the leads 228a and 228b, which acts as primary conductors can couple to the current sensor coil 602, which acts as a secondary winding, producing a significant error signal. The present disclosure provides for systems and methods for reducing the error signal due to voltage coupling between the active leads 228a and 228b and the current sensor coil 602. In particular, the present disclosure provides for specific arrangement of the active and/or return leads 228a, 228b relative to the current sensor coil 602 such that the undesired voltage signal is coupled as a common-mode signal and is then cancelled or reduced by the common rejection capabilities of the conditioning circuit 650. The present disclosure also provides for shielding the current sensor coil 602 to minimize coupling of the voltage signal. In embodiments, any combinations of arrangement of the active and/or return leads 228a, 228b and/or shielding may be utilized to minimize coupling of the voltage signal.

Figure 21:
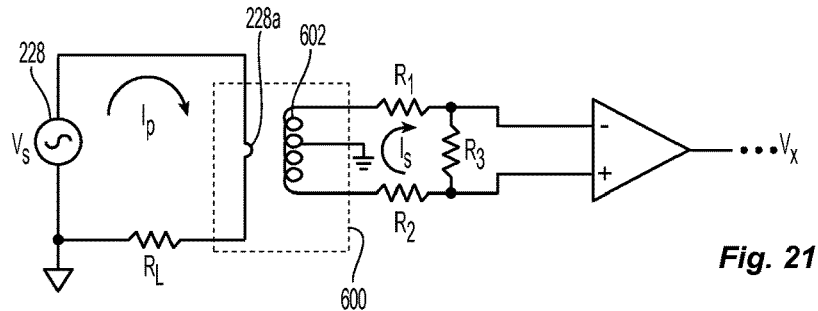
FIG. 21 is a schematic diagram of the current sensor of FIG. 18 according to the present disclosure.
Figure 22:
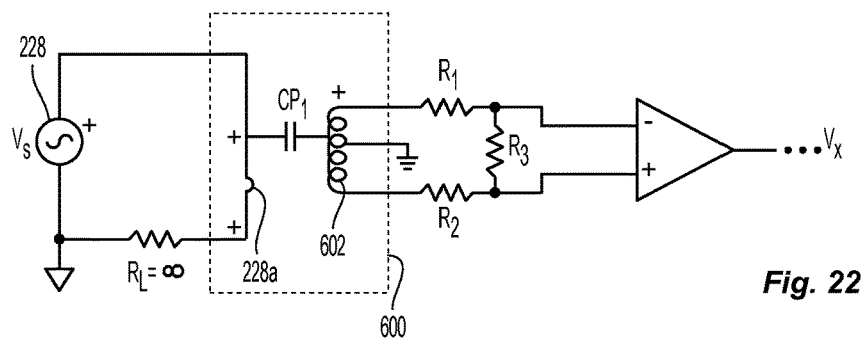
FIG. 22 is a schematic diagram of the current sensor of FIG. 18 with parasitic capacitive coupling according to the present disclosure.

With reference to FIGS. 21 and 22, the voltage coupling due to parasitic capacitance is described. FIGS. 21 and 22 illustrate the generator 200 including the RF amplifier 228 supplying RF current, Ip, through the active lead 228a with the current sensor coil 602 sensing the primary current, Ip, passing therethrough. The primary current, Ip, induces a secondary current, Is, in the current sensor coil 602, which develops a voltage, Vo.

In situations where the voltage at the active lead 228a is relatively large but the primary current, Ip, is low (e.g., near zero), the resulting Vo should also be near zero. With reference to FIG. 22, the high voltage capacitively couples from the active lead 228a to the current sensor coil 602, as represented schematically by a parasitic capacitance Cp1, which produces an erroneous output voltage.

Figure 23:
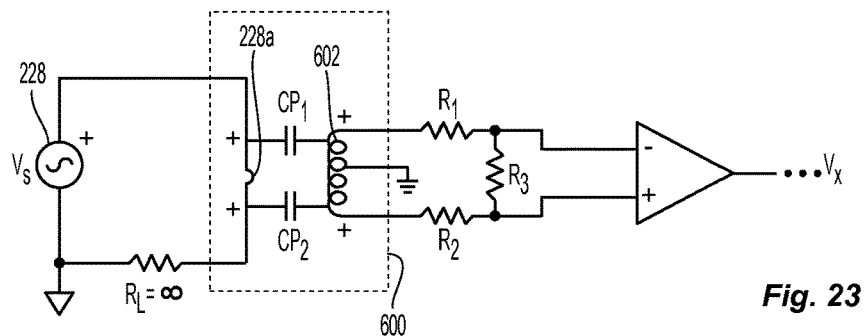
FIG. 23 is a schematic diagram of the current sensor of FIG. 18 with balanced out parasitic capacitive coupling according to the present disclosure.

FIG. 23 shows an embodiment of the present disclosure for reducing or eliminating erroneous output voltage signal output by the conditioning circuit 650. The present disclosure provides for a system of positioning the active leads 228a and/or return leads 228b in such a way as to balance the capacitive coupling therefrom to the current sensor coil 602. The conditioning circuit 650 then reduces the erroneous output voltage due to its common-mode rejection capability.

The active lead 228a is passed through the current sensor coil 602 to generate a second parasitic coupling capacitance, Cp2, which is also coupled to the current sensor coil 602. In particular, the capacitances Cp1 and Cp2 are coupled symmetrically about the sensor current sensor coil 602. The capacitance Cp2 couples a voltage from the active lead 228a to the current sensor coil 602 similarly to the capacitance Cp1, thereby balancing the circuit such that the resulting voltage is a common-mode voltage, which is then rejected by the conditioning circuit 650.

Figure 24:
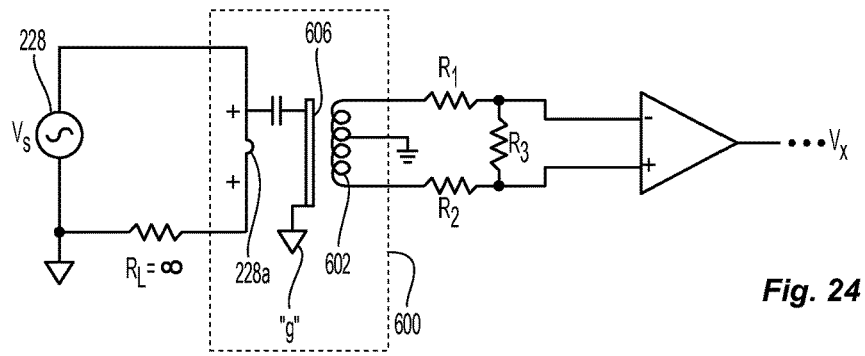
FIG. 24 is a schematic diagram of the current sensor of FIG. 18 having a shielding member according to the present disclosure.

FIG. 24 shows another embodiment of the present disclosure for reducing or eliminating erroneous output voltage by the conditioning circuit 650. The current sensor 600 includes one or more shielding members 606 disposed between the active leads 228a and the current sensor coil 602 to prevent or reduce the voltage coupling from active lead 228a to current sensor coil 602.

FIGS. 25A-E show an embodiment of the current sensor 600 including a circular current sensor coil 602 disposed on a printed circuit board (PCB) 601, which may be formed using the techniques described above with respect to the current sensor coil 302 of FIGS. 5-9. The current sensor 600 includes one or more active leads 228a, 228c and return leads 228b, 228d passing through an opening 603 of the current sensor coil 602. The leads 228a, 228b, 228c, 228d may be any suitable conductive leads (e.g., wires) having an insulating sheath. In embodiments, the leads 228a, 228b, 228c, 228d may be printed as conductive traces on the PCB 601 and passed through the current sensor coil 602 as vias, such as traces 408a and 408f and via 409a as described above with respect to FIGS. 5 and 9.

Figure 25E:
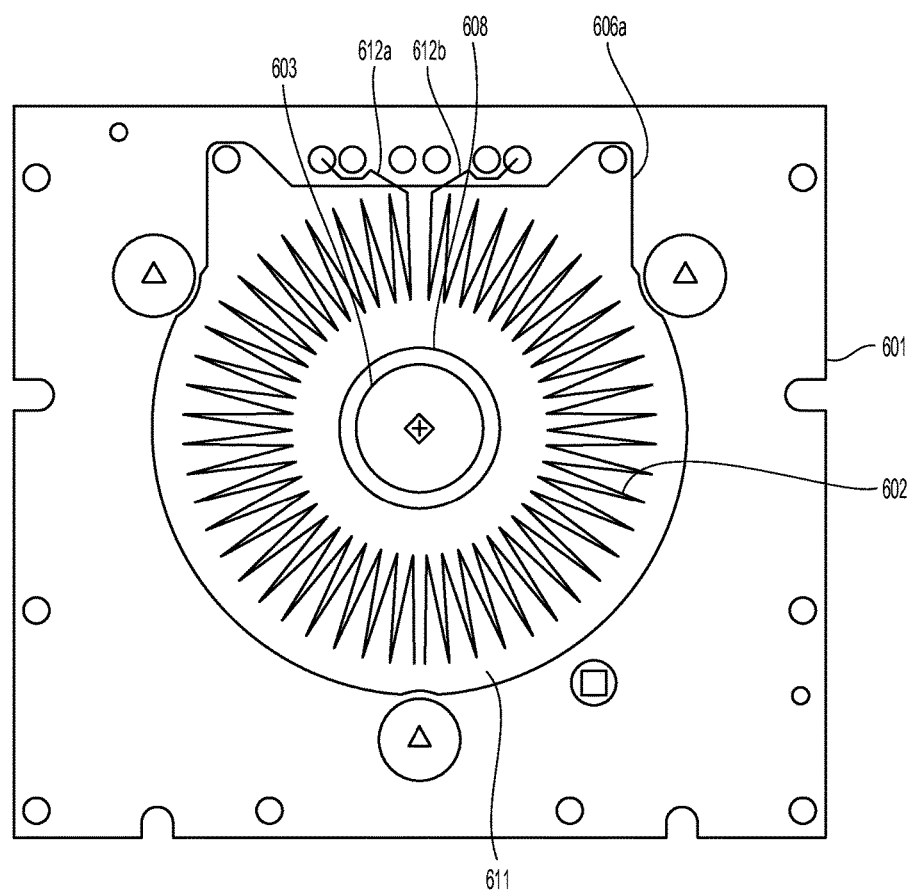
FIG. 25E is a plan view of the current sensor coil of FIG. 25A according to the present disclosure.

The current sensor 600 also includes a pair of shielding members 606a and 606b disposed over upper and lower surfaces of the current sensor coil 602. With reference to FIG. 25E, the shielding member 606a is shown and described, which is substantially similar to the shielding member 606b. The shielding member 606a is formed from a conductive material and is coupled to a ground "g" as shown in FIG. 24. The shielding member 606a includes an opening 608 therethrough for passage of leads 228a, 228b, 228c, 228d. The shielding member 606a is configured and dimensioned to substantially cover the current sensor coil 602. Since the current sensor coil 602 is disposed on the PCB 601, the shielding members 606a and 606b may be substantially flat. The shielding member 606a may be a discrete conductive layer attached to the PCB 601 on which the current sensor coil 602 is disposed using any suitable fasteners, adhesives, and combinations thereof.

In embodiments, the shielding members 606a, 606b, may be formed as layers on the PCB 601 as shown in FIG. 25E. As a result, the PCB 601 may include additional dielectric layers (e.g., outer dielectric layers) to accommodate the shielding members 606a, 606b as integrated layers. The shielding members 606a, 606b may be printed as a conductive layer on the PCB 601 as described above with respect to the printing of the current sensor coil 302. This configuration may be used in embodiments in which the leads 228a, 228b, 228c, 228d are formed as vias and traces. In particular, an additional dielectric layer may be disposed on top of the conductive trace 408b (FIG. 8), on top of which the shielding member 606a is then formed, as well as below conductive trace 408e (FIG. 8), below which the shielding member 606b is then formed.

The current sensor 600 also includes a pair of opposing spacers 610a and 610b. The spacers 610a and 610b are formed from a dielectric material and when assembled define an opening therethrough which aligns with the opening 603 of the current sensor coil 602. The leads 228a, 228b, 228c, 228d are wrapped around and through the spacers 610a and 610b as shown in FIG. 25D to maintain the leads 228a, 228b, 228c, 228d in a predetermined spatial relationship relative to themselves and the current sensor coil 602 to cancel and/or reduce the effects of parasitic capacitance as described above. The current sensor 600 also includes a pair of opposing housing portions 630a, 630b enclosing the interior components of the current sensor 600. The housing portions 630a, 630b also secure leads 228a, 228b, 228c, 228d relative to each other and the current sensor coil 602.

With reference to FIGS. 26A-31C, embodiments of a single-wire orientation of the active lead 228a about the current sensor coil 602 are shown. The coil 602 includes forming an inner coil 605 and an outer coil 607. With specific reference to FIG. 26A, the current sensor coil 602 at a first end 609 includes two terminals 612a and 612b coupled to the outer coil 607 and the third terminal 612c coupled the inner coil 605. The third terminal 612C also couples the inner coil 605 to the ground at the first end 609. The inner coil 605 center taps the outer coil 607 at a second end 611 as described in further detail below with respect to FIGS. 26B and 26C.

With continued reference to FIG. 26A, the outer coil 607 includes a semi-circular first portion 607a and a semi-circular second portion 607b and the inner coil 605 includes a semi-circular first portion 605a and a semi-circular second portion 605b. The first and second portions 605a, 605b and 607a, 607b are disposed symmetrically (e.g., on left and right sides) about an axis "X-X" defined between diametrically opposed (e.g., 180° apart) first and second ends 609 and 611 of the current sensor coil 602, respectively.

With reference to FIGS. 26B and 26C, enlarged schematic views of the first and second ends 609 and 611 of the current sensor coil 602, respectively, are shown. The first portion 607a of the outer coil 607 is coupled between the first terminal 612a on top (e.g., at first end 609) and a first connection 611a of the first portion 605a of the inner coil 605 on the bottom (e.g., at second end 611). The second portion coil 607b of the outer coil 607 is coupled between the second terminal 612b on top (e.g., at first end 609) and a second connection 611b of the second portion 605b of the inner coil 605 on bottom (e.g., at second end 611). Each of the first and second portions 605a, 605b of the inner coil 605 is coupled between the third terminal 612c at the first end 609 of the current sensor coil 602 and their respective connections 611a, 611b at second end 611 of the current sensor coil 602.

Figure 26D:
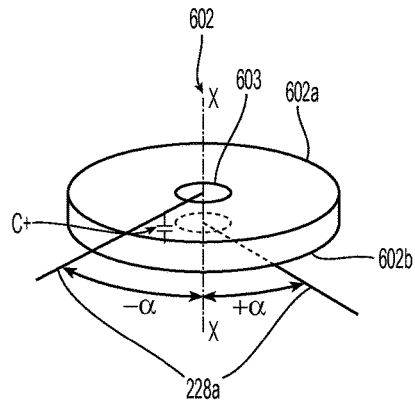
FIG. 26D is a perspective, schematic view of the current sensor coil of FIG. 26A according to the present disclosure.
Figure 26E:
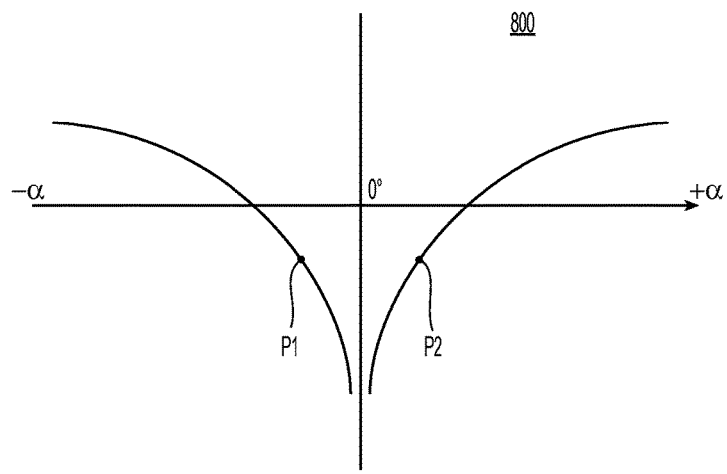
FIG. 26E is a plot of an erroneous error signal as function of wire position of the current sensor coil of FIG. 26A as a function of an angle of leads passing therethrough according to the present disclosure.
Figure 26F:
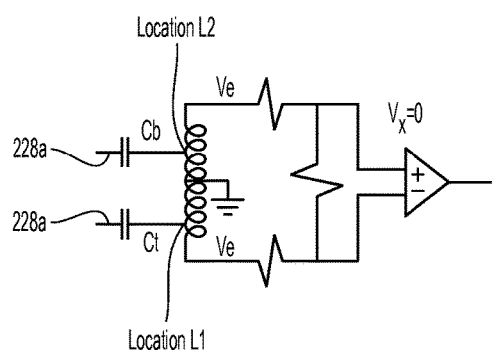
FIG. 26F is a schematic diagram of the current sensor coil of FIG. 26A with parasitic capacitive coupling according to the present disclosure.

With reference to FIGS. 26D-F, a top portion of the active lead 228a is passed across a top surface 602a of the current sensor coil 602 and is disposed in a $-\alpha$ orientation, e.g., at an angle $\alpha$ relative to the axis "X-X." A bottom portion of active lead 228 extends through the opening 603 and across a bottom surface 602b of the current sensor coil 602 such that the bottom portion of active lead 228a is disposed in a $+\alpha$ orientation relative to the axis "X-X." It should be appreciated that movement in the $-\alpha$ direction along sensor coil 602 in FIG. 26D corresponds to movement in a downwardly direction along sensor coil 602 in FIG. 26F. Similarly, movement in the $+\alpha$ direction along sensor coil 602 in FIG. 26D corresponds to movement in an upwardly direction along sensor coil 602 in FIG. 26F.

The active lead 228a is disposed symmetrically about the axis "X-X" across the top and bottom surfaces 602a, 602b of the current sensor coil 602 such that the erroneous voltage signals, Ve, generated by the active lead 228a are canceled out. In particular, the portion of the active lead 228a disposed on the top surface 602a and the portion of the active lead 228a disposed on the bottom surface 602b are symmetrical about the axis "X-X."

The top portion of active lead 228a creates capacitive coupling or parasitic capacitance $C_t$ within the sensor soil 602 at location L1 (FIG. 26F). Similarly, the bottom portion of active lead 228a creates capacitive coupling or parasitic capacitance $C_b$ within sensor coil 602 at location L2 (FIG. 26F). Two operating points identified as "P1" and "P2" in FIG. 26E correspond to locations L1 and L2, respectively, in FIG. 26F. An error signal Ve is generated at location L1 and an error signal Ve is created at location L2. The differential amplifier takes the difference of these two error signals to generate an output of zero (i.e., Vx=Ve−Ve=0). With the inner coil 605 attached at the center of the outer coil 607, the capacitive coupling is balanced, causing the erroneous signal to be a common-mode voltage. Thus the differential circuitry causes the erroneous error signal to be removed. Accordingly, the embodiments of sensor circuit 602 provided above are balanced, have shielding, or are both balanced and have shielding such that the circuits produce little to no output signal Vx when there is no input current.

FIG. 26E shows a plot 800 illustrating a logarithmic ratio of output voltage Vx of the amplifier to the voltage on active lead 228a vs. angular location. The logarithmic ratio is calculated using the equation of 20 Log(|V$_x$|/|V$_{in}$|), in which Vx is the output of the differential amplifier and V$_{in}$ is the voltage on active lead 228a. Operating points "P1" and "P2" correspond to the locations L1 and L2 of the parasitic capacitances $C_t$, $C_b$ shown in FIG. 26F. The slope of the graph illustrates sensitivity, i, of the output voltage Vx of the differential amplifier as a function of positional angle between the axis "X-X" and the active lead 228a. As the angle increases from about 0° to about 90°, the sensitivity to erroneous voltage signals Ve of the current sensor coil 602 decreases. This relationship may be used to locate the active lead 228a relative to the axis "X-X" to obtain the most accurate reading of the current passing therethrough while minimizing the interference caused by the erroneous voltage signals Ve.

With reference to FIGS. 27A-B, 28A-B, 29A-C, 30A-C, and 31A-C, multiple embodiments of single wire configurations of the sensor coil 602 are shown. With specific reference to FIGS. 27A and 27B, sensor coil 602 includes a length of wire, namely the inner coil 605, passing through the middle of the sensor coil 602 such that the wire extends from a first end 609 to a second end 611 of sensor coil 602. The top surface of sensor coil 602 in FIG. 27A corresponds to the left side of sensor coil 602 in FIG. 27B. Similarly, the bottom surface of sensor coil 602 in FIG. 27A corresponds to the right side of sensor coil 602 in FIG. 27B.

Figure 27A:
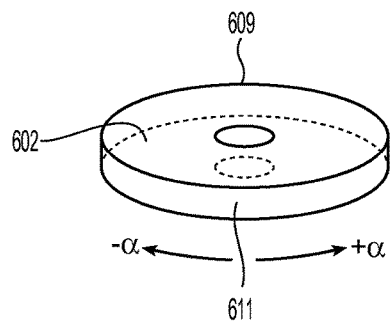
FIG. 27A is a perspective, schematic view of a current sensor coil according to another embodiment of the present disclosure.
Figure 27B:
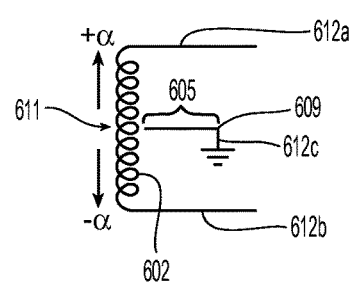
FIG. 27B is a schematic diagram of the current sensor of FIG. 27A according to the present disclosure.
Figure 28A:
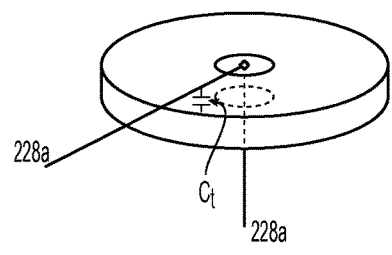
FIG. 28A is a perspective, schematic view of the current sensor coil according to another embodiment of the present disclosure.
Figure 28B:
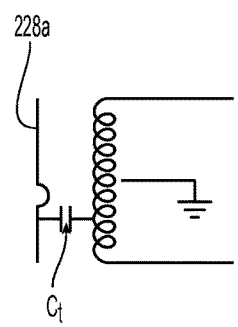
FIG. 28B is a schematic diagram of the current sensor of FIG. 28A with parasitic capacitive coupling according to the present disclosure.

With respect to FIG. 28A, sensor coil 602 is shown, differing from sensor coil 602 shown in FIG. 27A by the addition of wire 228a running through the central opening in sensor coil 602. Assuming there is no current traveling through the wire 228a, the output of the sensor coil 602 should be ideally zero. The wire 228a is in close proximity to the sensor coil 602 and will capacitively couple via Ct an undesired error voltage, Ve, from the wire 228a to the sensor coil 602. The position of wire 228a relative to the sensor coil 602 determines the location at which the error voltage is coupled, and thus affects how the circuit processes the signal. This, in turn, affects the output signal Vo.

FIGS. 29A-C, FIGS. 30A-C, and FIGS. 31A-C show additional single-wire configurations of the sensor coil 602. With specific reference to FIG. 29A, the wire 228a is routed on the top and the bottom of sensor coil 602. Thus, each of the top and bottom portions of wire 228a couples to the sensor coil 602 forming a parasitic capacitance $C_t$, $C_b$, as shown in FIG. 29C. Since both $C_t$ and $C_b$ are at 0 degrees relative to the axis "X-X," they are capacitvely coupled to the center tap of the sensor coil 602, which is grounded and therefore signal Ve is zero, hence, Vx is also zero. This corresponds to the operating points "P1" and "P2" shown in FIG. 29B representative of a low error signal. Although this configuration provides for a low error signal, any movement in α yields a large change in error voltage.

FIG. 30A shows both top and bottom portions of active lead 228a disposed in +α direction. As shown in FIG. 30C, the top and bottom portions of active lead 228a are capacitively coupled at the same location due to the overlap of the active lead 228a on the sensor coil 602, but off the center tap due to the placement of active lead 228a in FIG. 30A as compared to the configuration shown in FIGS. 29A-C. An error signal Ve, is coupled into the sensor coil 602 by each of the top and bottom portions of the active lead 228a. This corresponds to the operating points "P1" and "P2" shown in FIG. 30B representative of error signal. The error signal is coupled to the negative input of the amplifier, and produces an output of Vx=−2Ve, since two active leads 228a are coupling to the same location.

FIG. 31A shows the top and bottom portions of active lead 228a moved in the −α direction. The the top and bottom portions of active lead 228a are capacitively coupled at the same location due to the overlap of the active lead 228a on the sensor coil 602, but off the center tap due to the placement of active lead 228a in FIG. 31A as compared to the configuration shown in FIGS. 29A-C. An error signal Ve, is coupled into the sensor coil 602 by each of the top and bottom portions of the active lead 228a. This corresponds to the operating points "P1" and "P2" shown in FIG. 31B representative of error signal. The error signal is coupled to the positive input of the amplifier, and produces an output of Vx=+2Ve, since two active leads 228a are coupling to the same location.

Figure 32A:
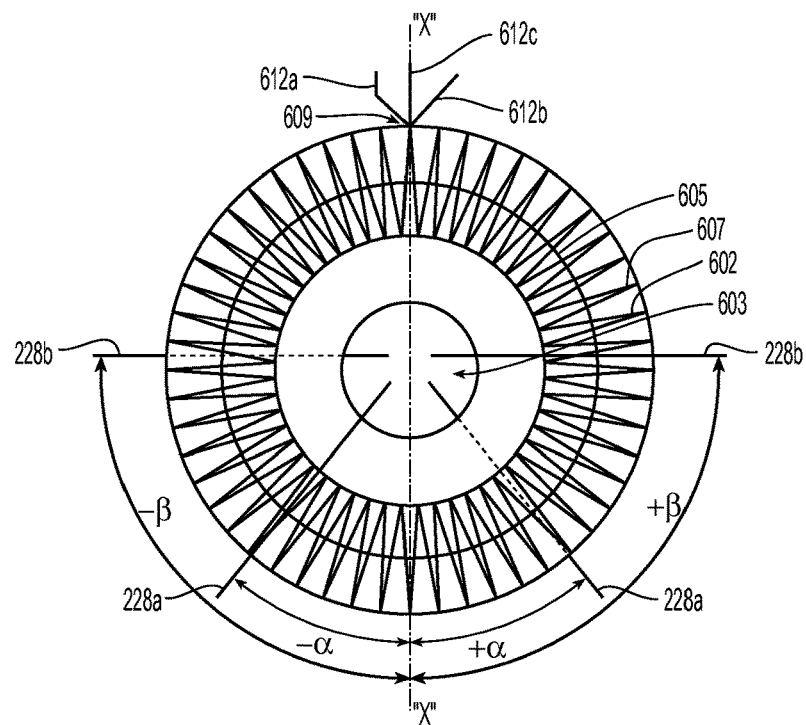
FIG. 32A is a partially-exposed, plan view of a current sensor coil of the current sensor according to another embodiment of the present disclosure.
Figure 32B:
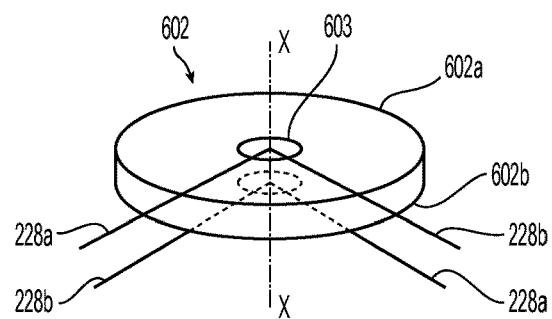
FIG. 32B is a perspective, schematic view of the current sensor of FIG. 32A according to the present disclosure.

With reference to FIGS. 32A and 32B, a two-wire orientation of the active lead 228a and return lead 228b about the current sensor coil 602 is shown schematically. The active and return leads 228a, 228b are passed across the top surface 602a of the current sensor coil 602, through the opening 603, and across the bottom surface 602b of the current sensor coil 602. The top and bottom portions of the active lead 228a are symmetrical about the axis "X-X" at a first angle, −α and +α, respectively, and the top and bottom portions of the return lead 228b are symmetrical about the axis "X-X" at a second angle, +β and −β, respectively. The active and return leads 228a, 228b may be disposed at an angle ±α, ±β, respectively, from about 0° to about 90° relative to the axis "X-X." In embodiments, angles ±α, ±β may be the same, as shown in FIG. 32B, or different, as shown in FIG. 32A.

With reference to FIG. 33, multiple active leads 228a and 228c and multiple return leads 228b and 228d may be used depending on the number of outputs within the generator 200, e.g., bipolar, monopolar, etc. The active and return leads 228a, 228c and 228b, 228d are also disposed in a symmetrical relationship (e.g., transverse to the axis "X-X") relative to each other about the axis "X-X," such that the erroneous voltage signals are cancelled.

In embodiments, any number of active and return leads 228a, 228c and 228b, 228d may be wrapped about the current sensor coil 602 as illustrated in FIG. 33. This configuration may include two pairs of active and return leads 228a, 228c, and 228b, 228d, which may be disposed in an overlapping relationship, such that active and return leads 228a, 228c and 228b, 228d, respectively are disposed over each other. This arrangement may be used with a differential-mode current transformer configuration.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A sensor for sensing current, the sensor comprising:
a current sensor coil defining an opening therethrough and including:
an outer coil;
a pair of first and second terminals coupled to the outer coil at a first end of the current sensor coil; and
an inner coil coupled to and disposed within the outer coil; and
at least one active lead and at least one return lead each passing through the opening of the current sensor coil, wherein the current sensor coil is configured to output a differential signal indicative of a current within the at least one active lead or the at least one return lead, the at least one active lead including:
a top portion extending parallel with and over a top surface of the current sensor coil at a first non-zero acute angle relative to an axis that extends through the first end of the current sensor coil and a center of the opening of the current sensor coil; and
a bottom portion extending parallel with and over a bottom surface of the current sensor coil at a second non-zero acute angle relative to the axis, the first and second angles being symmetrical relative to each other about the axis.

2. The sensor according to claim 1, further comprising:
a conditioning circuit configured to at least one of integrate, amplify, or filter the differential signal to output a processed signal indicative of the current.

3. The sensor according to claim 1, further comprising:
at least one shielding member disposed over the outer coil.

4. The sensor according to claim 3, wherein the current sensor coil is disposed within a printed circuit board.

5. The sensor according to claim 4, wherein the printed circuit board includes:
a plurality of outer conductive traces each being coupled to at least one of the active lead or the return lead, the plurality of outer conductive traces being interconnected by at least one via through the printed circuit board.

6. The sensor according to claim 5, wherein the printed circuit board includes:
a top dielectric layer;
a first dielectric intermediate layer;
a bottom dielectric layer; and
a second dielectric intermediate layer; and
wherein the outer coil includes:
a plurality of top conductive traces disposed between the top dielectric layer and the first dielectric intermediate layer of the printed circuit board;
a plurality of bottom conductive traces disposed between the bottom dielectric layer and the second dielectric intermediate layer of the printed circuit board, wherein the outer conductive traces are disposed over outer surfaces of the bottom and top dielectric layers; and
a plurality of inner and outer vias interconnecting the pluralities of top and bottom conductive traces.

7. The sensor according to claim 6, wherein the inner coil includes:
at least one conductive trace disposed within the outer coil and between the first and second dielectric intermediate layers of the printed circuit board.

8. The sensor according to claim 6, wherein the shielding member is disposed over an outer dielectric layer disposed over the outer surface of at least one of the top dielectric layer or the bottom dielectric layer.

9. The sensor according to claim 2, wherein the current sensor coil are has a second end disposed on an opposite side of the opening of the current sensor coil as the first end, each of the outer coil and the inner coil includes first and second portions, the first and second portions being separated at the second end of the current sensor coil.

10. The sensor according to claim 9, wherein the conditioning circuit is coupled to the first and second terminals, which are coupled to the respective first and second portions of the outer coil at the first end of the current sensor coil, and the first and second portions of the inner coil are coupled to a third ground terminal at the first end of the current sensor coil.

11. The sensor according to claim 10, wherein the first portions of the outer coil and the inner coil are coupled to each other at the second end and the second portions of the outer coil and the inner coil are coupled to each other at the second end.

12. The sensor according to claim 2, wherein the conditioning circuit is fully differential.

13. A sensor for sensing current, the sensor comprising:
a current sensor coil defining an opening therethrough and diametrically opposed first and second ends, the current sensor coil including:
an outer coil including a first semi-circular portion and a second semi-circular portion; and
an inner coil disposed within the outer coil and including a first semi-circular portion and a second semi-circular portion, wherein the first semi-circular portions and the second semi-circular portions of the inner and outer coils are separated at the second end; and
at least one active lead passing through the current sensor coil, wherein the current sensor coil is configured to output a signal indicative of a current within the at least one active lead, the at least one active lead including:
a top portion extending along a plane defined by a top surface of the first semi-circular portion of the outer coil at a first non-zero acute angle relative to an axis that extends through the first end of the current sensor coil and a center of the opening of the current sensor coil; and
a bottom portion extending along a plane defined by a bottom surface of the second semi-circular portion of the outer coil at a second non-zero acute angle relative to the axis, the first and second angles being symmetrical relative to each other about the axis.

14. The sensor according to claim 13, further comprising at least one shielding member disposed over the outer coil and defining a second opening therethrough in alignment with the opening of the current sensor coil.

15. The sensor according to claim 13, further comprising:
a conditioning circuit coupled to the inner and outer coils at the first end and configured to at least one of integrate, amplify, or filter a differential signal to output the signal indicative of the current.

16. The sensor according to claim 13, further comprising at least one return lead passing through the current sensor coil, wherein the current sensor coil is configured to output a second signal indicative of a current within the at least one return lead.

17. The sensor according to claim 16, wherein the at least one return lead includes:
- a top portion extending along the plane defined by the top surface of the first semi-circular portion of the outer coil; and
- a bottom portion extending along the plane defined by the bottom surface of the second semi-circular portion of the outer coil.

* * * * *